United States Patent
Jeschke et al.

(10) Patent No.: US 7,645,738 B2
(45) Date of Patent: Jan. 12, 2010

(54) 18-MEMBERED NITROBENZYL- AND AMINOBENZYL-SUBSTITUTED CYCLOHEXADEPSIPEPTIDES FOR CONTROLLING ENDOPARASITES AND A PROCESS FOR THEIR PREPARATION

(75) Inventors: Peter Jeschke, Bergisch Gladbach (DE); Achim Harder, Köln (DE)

(73) Assignee: Bayer Animal Health GmbH (DE)

( * ) Notice: Subject to any disclaimer, the term of this patent is extended or adjusted under 35 U.S.C. 154(b) by 268 days.

(21) Appl. No.: 10/582,555

(22) PCT Filed: Dec. 7, 2004

(86) PCT No.: PCT/EP2004/013896

§ 371 (c)(1),
(2), (4) Date: Jun. 4, 2007

(87) PCT Pub. No.: WO2005/063277

PCT Pub. Date: Jul. 14, 2005

(65) Prior Publication Data

US 2008/0026990 A1    Jan. 31, 2008

(30) Foreign Application Priority Data

Dec. 19, 2003   (DE) ................. 103 59 798

(51) Int. Cl.
*A61K 38/00*      (2006.01)
(52) U.S. Cl. ....................................... 514/9
(58) Field of Classification Search ........................ None
See application file for complete search history.

(56) References Cited

U.S. PATENT DOCUMENTS 5,589,503 A * 12/1996 Mencke et al. .............. 514/450

FOREIGN PATENT DOCUMENTS

| EP | 0 662 326 B1 | 7/1995 |
|---|---|---|
| EP | 0 664 297 B1 | 7/1995 |
| WO | WO 95/27498 | * 3/1995 |
| WO | WO 95/27498 | 10/1995 |
| WO | WO 96/38165 | 12/1996 |

* cited by examiner

*Primary Examiner*—Cecilia Tsang
*Assistant Examiner*—Thomas S Heard
(74) *Attorney, Agent, or Firm*—Jessica Monachello

(57) ABSTRACT

The invention relates to cyclic depsipeptides, especially 18-membered cyclohexadepsipeptides of general formula (I) and the salts thereof, wherein $R^1$ represents nitrobenzyl or R'R"N-benzyl—wherein R' and R" independently represent hydrogen, optionally substituted $C_1$-$C_4$-alkyl, formyl, $C_1$-$C_4$-alkoxy-$C_1$-$C_4$-alkyl, $C_1$-$C_4$-alkoxycarbonyl, or hydroxy-$C_1$-$C_2$-alkyl-sulfonyl-$C_1$-$C_2$-alkyl, or, together with the nitrogen atom to which they are bound, R' and R" form an optionally substituted monocyclic or polycyclic, optionally bridged and/or spirocyclic, saturated or unsaturated heterocycle containing between one and three other heteroatoms from the group of nitrogen, oxygen and sulphur, or R' and R" together form $C_3$-$C_5$-alkylene monocarbonyl or an optionally substituted diacyl radical of a $C_4$-$C_6$-dicarboxylic acid—and $R^2$, $R^3$ and $R^4$ independently represent $C_1$-$C_4$-alkyl. The invention also relates to the optical isomers and racemates of said cyclic depsipeptides, to a method for the production thereof, and to the use of the same for controlling endoparasites.

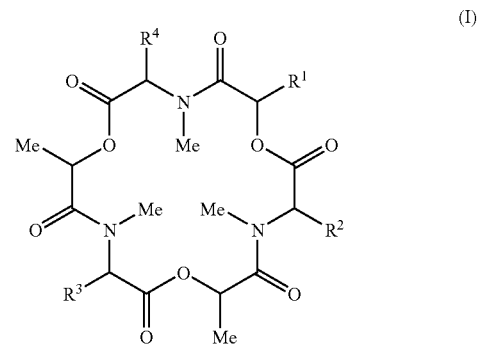

(I)

8 Claims, No Drawings

18-MEMBERED NITROBENZYL- AND AMINOBENZYL-SUBSTITUTED CYCLOHEXADEPSIPEPTIDES FOR CONTROLLING ENDOPARASITES AND A PROCESS FOR THEIR PREPARATION

The present invention relates to cyclic depsipeptides, in particular 18-membered cyclohexadepsipeptides, to a process for their preparation and to their use for controlling endoparasites.

Various cyclodepsipeptides having 18 ring atoms are already known as agents for controlling endoparasites (cf., for example, DE 4 317 458 A1, EP 669 343 A1, EP 658 551 A1).

However, at low application rates and concentrations, the activity of these prior-art compounds is not entirely satisfactory.

The present invention provides novel cyclic depsipeptides and processes for preparing the cyclic depsipeptides having amino acids and hydroxycarboxylic acids as ring building blocks and 18 ring atoms.

The invention also provides the use of cyclic depsipeptides comprising amino acids and hydroxycarboxylic acids as ring building blocks and 18 ring atoms as agents for controlling endoparasites.

The present invention relates in particular to:

1. Cyclic depsipeptides of the general formula (I) and salts thereof

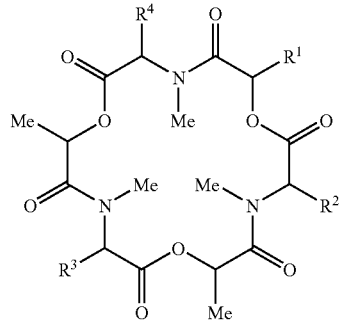

in which
R' represents nitrobenzyl or R'R"N-benzyl
where
R' and R" independently of one another each represent hydrogen, optionally substituted $C_1$-$C_4$-alkyl, formyl, $C_1$-$C_4$-alkoxy-$C_1$-$C_4$-alkyl, $C_1$-$C_4$-alkoxycarbonyl, hydroxy-$C_1$-$C_2$-alkylsulphonyl-$C_1$-$C_2$-alkyl
or
R' and R" together with the nitrogen atom to which they are attached form an optionally substituted mono- or polycyclic saturated or unsaturated heterocycle which is optionally bridged and/or spirocyclic and which contains 1 to 3 further heteroatoms from the group consisting of nitrogen, oxygen and sulphur, or R' and R" together form $C_3$-$C_5$-alkylenemonocarbonyl or an optionally substituted diacyl radical of a $C_4$-$C_6$-dicarboxylic acid, and $R^2$, $R^3$ and $R^4$ independently of one another represent $C_1$-$C_4$-alkyl, and optical isomers and racemates thereof.

2. The novel cyclic depsipeptides of the general formula (I) and salts thereof

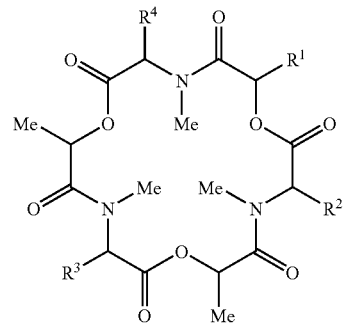

in which
$R^1$, $R^2$, $R^3$ and $R^4$ are as defined under item 1
are prepared by
a) in a first step, nitrating the cyclic depsipeptides of the general formula (II) and salts thereof

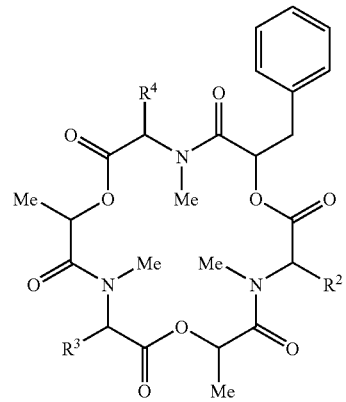

in which
$R^2$, $R^3$ and $R^4$ are as defined under item 1
in the presence of a nitrating agent and, if appropriate, in the presence of a diluent, and b) if appropriate, in a second step, reducing the nitro group in the cyclic depsipeptides of the general formula (III) or salts thereof obtained in this manner

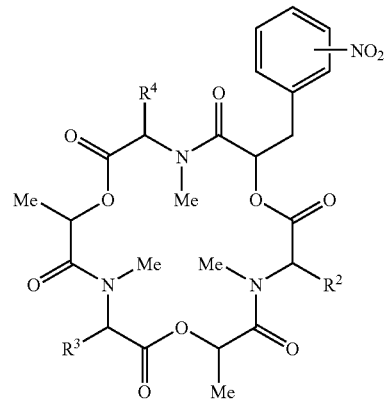

in which
$R^2$, $R^3$ and $R^4$ are as defined under item 1
in the presence of a reducing agent and, if appropriate, in the presence of a diluent, and c) if appropriate, in a third step, aminoalkylating the cyclic depsipeptides of the general formula (IV) and salts thereof

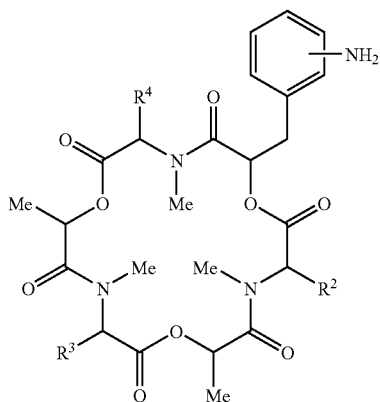
(IV)

in which
R², R³ and R⁴ are as defined under item 1
to introduce the radicals R' and R", in the presence of a suitable aldehyde and a reducing agent and, if appropriate, in the presence of a diluent, or
N-alkylating these depsipeptides in the presence of a suitable alkylating agent and a basic reaction auxiliary and, if appropriate, in the presence of a diluent, or
N-acylating these depsipeptides in the presence of a suitable acylating agent and a basic reaction auxiliary and, if appropriate, in the presence of a diluent.

Depending on the nature of the substituents, the compounds of the general formula (I) can be present as geometrical and/or optical isomer mixtures of varying compositions. The invention relates both to the pure isomers and to isomer mixtures.

Preference is given to cyclic depsipeptides comprising amino acids and hydroxycarboxylic acids as ring building blocks and 18 ring atoms of the general formula (I) and salts thereof

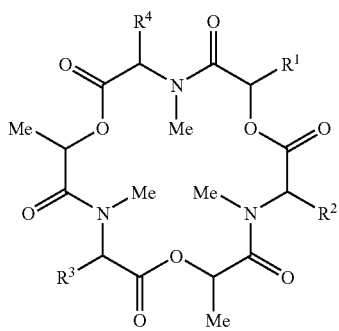
(I)

in which
R¹ represent nitrobenzyl or R'R"N-benzyl
where
R' and R" independently of one another each represent hydrogen, $C_1$-$C_3$-alkyl, in particular methyl, ethyl, $C_1$-$C_3$-alkoxy-$C_1$-$C_3$-alkyl, in particular methoxyethyl, 2-hydroxyethylsulphonyl-$C_1$-$C_2$-alkyl, in particular 2-hydroxyethylsulphonylethyl or R' and R" together with the nitrogen atom to which they are attached represent N-pyrrolidino, N-piperidino, N-piperazino, N-morpholino, N-2,6-dimethylmorpholino, N-thiomorpholino, N-pyrazolo, N-imidazolo, 2-oxopyrrolidin-1-yl, 2-oxopiperidin-1-yl, 2-oxoazepan-1-ylmethyl, succinimino, maleinimino or glutarimino,
R², R³ and R⁴ independently of one another represent $C_1$-$C_4$-alkyl,
and optical isomers and racemates thereof.

Particular preference is given to cyclic depsipeptides comprising amino acids and hydroxycarboxylic acids as ring building blocks and 18 ring atoms of the general formula (I) and salts thereof

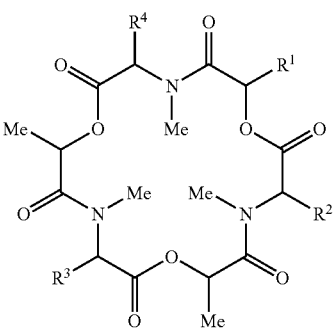
(I)

in which
R¹ represents 4-nitrobenzyl, 4-aminobenzyl, 4-morpholinobenzyl, 4-hydroxyethylsulphonylethylaminobenzyl,
R² and R⁴ independently of one another represent $C_1$-$C_4$-alkyl, in particular methyl, isopropyl, isobutyl or sec-butyl,
R³ represents methyl or ethyl, and optical isomers and racemates thereof.

Very particular preference is given to cyclic depsipeptides comprising amino acids and hydroxycarboxylic acids as ring building blocks and 18 ring atoms of the general formula (I) and salts thereof

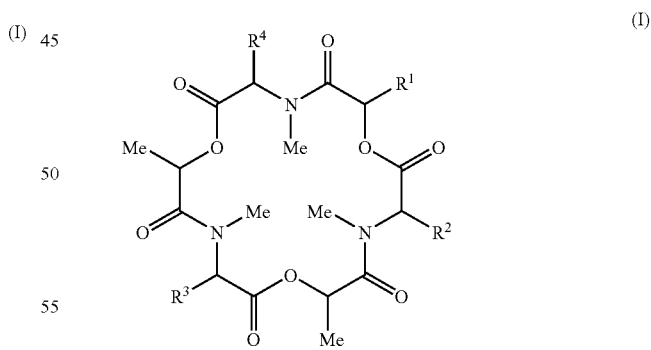
(I)

in which
R¹ represents 4-nitrobenzyl, 4-aminobenzyl, 4-morpholinobenzyl, 4-hydroxyethylsulphonylethylaminobenzyl,
R² and R⁴ represent sec-butyl,
R³ represents methyl, and optical isomers and racemates thereof.

The cyclic depsipeptides according to the invention and their acid addition salts and metal salt complexes have good endoparasiticidal, in particular anthelmintic, action and can preferably be used in the field of veterinary medicine.

The cyclic depsipeptides of the general formula (I) according to the invention and salts thereof contain one or more centres of chirality and may therefore be present as pure stereoisomers or in the form of various mixtures of enantiomers and diastereomers which, if required, may be separated in a manner known per se or else may be prepared by stereoselective reactions in combination with the use of stereochemically pure starting materials.

However, preference is given to employing the optically active stereoisomeric forms of the compounds of the general formula (I) and salts thereof according to the invention. Particular preference is given to the cyclic depsipeptides constructed of (S)-configured amino acids (L form) and (R)-configured hydroxycarboxylic acids (D form) as ring building blocks.

The invention therefore provides the pure enantiomers and diastereomers and also mixtures thereof for controlling endoparasites, in particular in the fields of medicine and veterinary medicine.

Suitable salts of the depsipeptides of the general formula (I) include conventional non-toxic salts, i.e. salts with appropriate bases and salts with added acids. Preference is given to salts with inorganic bases, such as alkali metal salts, for example sodium salts, potassium salts or caesium salts, alkaline earth metal salts, for example calcium salts or magnesium salts, ammonium salts, salts with organic bases and also with inorganic amines, for example triethylammonium salts, dicyclohexylammonium salts, N,N'-dibenzylethylenediammonium salts, pyridinium salts, picolinium salts or ethanolammonium salts, salts with inorganic acids, for example hydrochlorides, hydrobromides, dihydrosulphates, trihydrosulphates, or phosphates, salts with organic carboxylic acids or organic sulphonic acids, for example formates, acetates, trifluoroacetates, maleates, tartrates, methanesulphonates, benzenesulphonates or para-toluenesulphonates, salts with basic amino acids, for example arginates, aspartates or glutamates, and the like.

The salts of the depsipeptides furthermore also include metal salt complexes, for example alkali metal salts, such as sodium salts, potassium salts or caesium salts, or alkaline earth metal salts, such as, for example, calcium salts or magnesium salts.

As solids, the depsipeptides or salts thereof may also be present in the form of solvates, in particular hydrates. These are also embraced by the invention.

Specifically, mention may be made of the following cyclodepsipeptides having 18 ring atoms:

cyclo(-N-methyl-L-alanyl-D-lactyl-N-methyl-L-isoleucyl-D-2-nitro-phenyllactyl-N-methyl-L-isoleucyl-D-lactyl-),
cyclo(-N-methyl-L-alanyl-D-lactyl-N-methyl-L-isoleucyl-D-3-nitro-phenyllactyl-N-methyl-L-isoleucyl-D-lactyl-),
cyclo(-N-methyl-L-alanyl-D-lactyl-N-methyl-L-isoleucyl-D-4-nitro-phenyllactyl-N-methyl-L-isoleucyl-D-lactyl-),
cyclo(-N-methyl-L-alanyl-D-lactyl-N-methyl-L-isoleucyl-D-2-amino-phenyllactyl-N-methyl-L-isoleucyl-D-lactyl-),
cyclo(-N-methyl-L-alanyl-D-lactyl-N-methyl-L-isoleucyl-D-3-amino-phenyllactyl-N-methyl-L-isoleucyl-D-lactyl-),
cyclo(-N-methyl-L-alanyl-D-lactyl-N-methyl-L-isoleucyl-D-4-amino-phenyllactyl-N-methyl-L-isoleucyl-D-lactyl-),
cyclo(-N-methyl-L-alanyl-D-lactyl-N-methyl-L-isoleucyl-D-3-morpholino-phenyl-lactyl-N-methyl-L-isoleucyl-D-lactyl-),
cyclo(-N-methyl-L-alanyl-D-lactyl-N-methyl-L-isoleucyl-D-4-morpholino-phenyl-lactyl-N-methyl-L-isoleucyl-D-lactyl-),
cyclo(-N-methyl-L-alanyl-D-lactyl-N-methyl-L-isoleucyl-D-3-(2-hydroxyethylsulphonyl-ethylamino-phenyl)lactyl-N-methyl-L-isoleucyl-D-lactyl-),
cyclo(-N-methyl-L-alanyl-D-lactyl-N-methyl-L-isoleucyl-D-4-(2-hydroxyethylsulphonyl-ethylamino-phenyl)lactyl-N-methyl-L-isoleucyl-D-lactyl-),
cyclo(-N-methyl-L-alanyl-D-lactyl-N-methyl-L-valinyl-D-2-nitro-phenyllactyl-N-methyl-L-isoleucyl-D-lactyl-),
cyclo(-N-methyl-L-alanyl-D-lactyl-N-methyl-L-valinyl-D-3-nitro-phenyllactyl-N-methyl-L-isoleucyl-D-lactyl-),
cyclo(-N-methyl-L-alanyl-D-lactyl-N-methyl-L-valinyl-D-4-nitro-phenyllactyl-N-methyl-L-isoleucyl-D-lactyl-),
cyclo(-N-methyl-L-alanyl-D-lactyl-N-methyl-L-valinyl-D-2-amino-phenyllactyl-N-methyl-L-isoleucyl-D-lactyl-),
cyclo(-N-methyl-L-alanyl-D-lactyl-N-methyl-L-valinyl-D-3-amino-phenyllactyl-N-methyl-L-isoleucyl-D-lactyl-),
cyclo(-N-methyl-L-alanyl-D-lactyl-N-methyl-L-valinyl-D-4-amino-phenyllactyl-N-methyl-L-isoleucyl-D-lactyl-),
cyclo(-N-methyl-L-alanyl-D-lactyl-N-methyl-L-valinyl-D-3-morpholino-phenyllactyl-N-methyl-L-isoleucyl-D-lactyl-),
cyclo(-N-methyl-L-alanyl-D-lactyl-N-methyl-L-valinyl-D-4-morpholino-phenyllactyl-N-methyl-L-isoleucyl-D-lactyl-),
cyclo(-N-methyl-L-alanyl-D-lactyl-N-methyl-L-valinyl-D-3-(2-hydroxyethylsulphonyl-ethylamino-phenyl)lactyl-N-methyl-L-isoleucyl-D-lactyl-),
cyclo(-N-methyl-L-alanyl-D-lactyl-N-methyl-L-valinyl-D-4-(2-hydroxyethylsulphonyl-ethylamino-phenyl)lactyl-N-methyl-L-isoleucyl-D-lactyl-),
cyclo(-N-methyl-L-2-amino-butyl-D-lactyl-N-methyl-L-isoleucyl-D-2-nitro-phenyllactyl-N-methyl-L-isoleucyl-D-lactyl-),
cyclo(-N-methyl-L-2-amino-butyl-D-lactyl-N-methyl-L-isoleucyl-D-3-nitro-phenyllactyl-N-methyl-L-isoleucyl-D-lactyl-),
cyclo(-N-methyl-L-2-amino-butyl-D-lactyl-N-methyl-L-isoleucyl-D-4-nitro-phenyllactyl-N-methyl-L-isoleucyl-D-lactyl-),
cyclo(-N-methyl-L-2-amino-butyl-D-lactyl-N-methyl-L-isoleucyl-D-2-amino-phenyllactyl-N-methyl-L-isoleucyl-D-lactyl-),
cyclo(-N-methyl-L-2-amino-butyl-D-lactyl-N-methyl-L-isoleucyl-D-3-amino-phenyllactyl-N-methyl-L-isoleucyl-D-lactyl-),
cyclo(-N-methyl-L-2-amino-butyl-D-lactyl-N-methyl-L-isoleucyl-D-4-amino-phenyllactyl-N-methyl-L-isoleucyl-D-lactyl-),
cyclo(-N-methyl-L-2-amino-butyl-D-lactyl-N-methyl-L-isoleucyl-D-3-morpholino-phenyllactyl-N-methyl-L-isoleucyl-D-lactyl-),
cyclo(-N-methyl-L-2-amino-butyl-D-lactyl-N-methyl-L-isoleucyl-D-4-morpholino-phenyllactyl-N-methyl-L-isoleucyl-D-lactyl-),
cyclo(-N-methyl-L-2-amino-butyl-D-lactyl-N-methyl-L-isoleucyl-D-3-(2-hydroxyethylsulphonyl-ethylamino-phenyl)lactyl-N-methyl-L-isoleucyl-D-lactyl-),
cyclo(-N-methyl-L-2-amino-butyl-D-lactyl-N-methyl-L-isoleucyl-D-4-(2-hydroxyethylsulphonyl-ethylamino-phenyl)lactyl-N-methyl-L-isoleucyl-D-lactyl-),
cyclo(-N-methyl-L-2-amino-butyl-D-lactyl-N-methyl-L-valinyl-D-2-nitro-phenyllactyl-N-methyl-L-isoleucyl-D-lactyl-), cyclo(-N-methyl-L-2-amino-butyl-D-lactyl-N-methyl-L-valinyl-D-3-nitro-phenyllactyl-N-methyl-L-isoleucyl-D-lactyl-),
cyclo(-N-methyl-L-2-amino-butyl-D-lactyl-N-methyl-L-valinyl-D-4-nitro-phenyllactyl-N-methyl-L-isoleucyl-D-lactyl-),
cyclo(-N-methyl-L-2-amino-butyl-D-lactyl-N-methyl-L-valinyl-D-2-amino-phenyllactyl-N-methyl-L-isoleucyl-D-lactyl-),
cyclo(-N-methyl-L-2-amino-butyl-D-lactyl-N-methyl-L-valinyl-D-3-amino-phenyllactyl-N-methyl-L-isoleucyl-D-lactyl-),
cyclo(-N-methyl-L-2-amino-butyl-D-lactyl-N-methyl-L-valinyl-D-4-amino-phenyllactyl-N-methyl-L-isoleucyl-D-lactyl-),
cyclo(-N-methyl-L-2-amino-butyl-D-lactyl-N-methyl-L-valinyl-D-3-morpholino-phenyllactyl-N-methyl-L-isoleucyl-D-lactyl-),
cyclo(-N-methyl-L-2-amino-butyl-D-lactyl-N-methyl-L-valinyl-D-4-morpholino-phenyllactyl-N-methyl-L-isoleucyl-D-lactyl-),
cyclo(-N-methyl-L-2-amino-butyl-D-lactyl-N-methyl-L-valinyl-D-3-(2-hydroxyethylsulphonyl-ethylamino-phenyl)lactyl-N-methyl-L-isoleucyl-D-lactyl-),
cyclo(-N-methyl-L-2-amino-butyl-D-lactyl-N-methyl-L-valinyl-D-4-(2-hydroxyethylsulphonyl-ethylamino-phenyl)lactyl-N-methyl-L-isoleucyl-D-lactyl-),
cyclo(-N-methyl-L-alanyl-D-lactyl-N-methyl-L-isoleucyl-D-2-nitro-phenyllactyl-N-methyl-L-valinyl-D-lactyl-),
cyclo(-N-methyl-L-alanyl-D-lactyl-N-methyl-L-isoleucyl-D-3-nitro-phenyllactyl-N-methyl-L-valinyl-D-lactyl-),
cyclo(-N-methyl-L-alanyl-D-lactyl-N-methyl-L-isoleucyl-D-4-nitro-phenyllactyl-N-methyl-L-valinyl-D-lactyl-),
cyclo(-N-methyl-L-alanyl-D-lactyl-N-methyl-L-isoleucyl-D-2-amino-phenyllactyl-N-methyl-L-valinyl-D-lactyl-),
cyclo(-N-methyl-L-alanyl-D-lactyl-N-methyl-L-isoleucyl-D-3-amino-phenyllactyl-N-methyl-L-valinyl-D-lactyl-),
cyclo(-N-methyl-L-alanyl-D-lactyl-N-methyl-L-isoleucyl-D-4-amino-phenyllactyl-N-methyl-L-valinyl-D-lactyl-),
cyclo(-N-methyl-L-alanyl-D-lactyl-N-methyl-L-isoleucyl-D-3-morpholino-phenyllactyl-N-methyl-L-valinyl-D-lactyl-),
cyclo(-N-methyl-L-alanyl-D-lactyl-N-methyl-L-isoleucyl-D-4-morpholino-phenyllactyl-N-methyl-L-valinyl-D-lactyl-),
cyclo(-N-methyl-L-alanyl-D-lactyl-N-methyl-L-isoleucyl-D-3-(2-hydroxyethylsulphonyl-ethylamino-phenyl)lactyl-N-methyl-L-valinyl-D-lactyl-),
cyclo(-N-methyl-L-alanyl-D-lactyl-N-methyl-L-isoleucyl-D-4-(2-hydroxyethylsulphonyl-ethylamino-phenyl)lactyl-N-methyl-L-valinyl-D-lactyl-),
cyclo(-N-methyl-L-alanyl-D-lactyl-N-methyl-L-valinyl-D-2-nitro-phenyllactyl-N-methyl-L-valinyl-D-lactyl-),
cyclo(-N-methyl-L-alanyl-D-lactyl-N-methyl-L-valinyl-D-3-nitro-phenyllactyl-N-methyl-L-valinyl-D-lactyl-),
cyclo(-N-methyl-L-alanyl-D-lactyl-N-methyl-L-valinyl-D-4-nitro-phenyllactyl-N-methyl-L-valinyl-D-lactyl-),
cyclo(-N-methyl-L-alanyl-D-lactyl-N-methyl-L-valinyl-D-2-amino-phenyllactyl-N-methyl-L-valinyl-D-lactyl-),
cyclo(-N-methyl-L-alanyl-D-lactyl-N-methyl-L-valinyl-D-3-amino-phenyllactyl-N-methyl-L-valinyl-D-lactyl-),
cyclo(-N-methyl-L-alanyl-D-lactyl-N-methyl-L-valinyl-D-4-amino-phenyllactyl-N-methyl-L-valinyl-D-lactyl-),
cyclo(-N-methyl-L-alanyl-D-lactyl-N-methyl-L-valinyl-D-3-morpholino-phenyllactyl-N-methyl-L-valinyl-D-lactyl-),
cyclo(-N-methyl-L-alanyl-D-lactyl-N-methyl-L-valinyl-D-4-morpholino-phenyllactyl-N-methyl-L-valinyl-D-lactyl-),
cyclo(-N-methyl-L-alanyl-D-lactyl-N-methyl-L-valinyl-D-3-(2-hydroxyethylsulphonyl-ethylamino-phenyl)lactyl-N-methyl-L-valinyl-D-lactyl-),
cyclo(-N-methyl-L-alanyl-D-lactyl-N-methyl-L-valinyl-D-4-(2-hydroxyethylsulphonyl-ethylamino-phenyl)lactyl-N-methyl-L-valinyl-D-lactyl-),
cyclo(-N-methyl-L-alanyl-D-lactyl-N-methyl-L-isoleucyl-D-2-nitro-phenyllactyl-N-methyl-L-alanyl-D-lactyl-),
cyclo(-N-methyl-L-alanyl-D-lactyl-N-methyl-L-isoleucyl-D-3-nitro-phenyllactyl-N-methyl-L-alanyl-D-lactyl-),
cyclo(-N-methyl-L-alanyl-D-lactyl-N-methyl-L-isoleucyl-D-4-nitro-phenyllactyl-N-methyl-L-alanyl-D-lactyl-),
cyclo(-N-methyl-L-alanyl-D-lactyl-N-methyl-L-isoleucyl-D-2-amino-phenyllactyl-N-methyl-L-alanyl-D-lactyl-),
cyclo(-N-methyl-L-alanyl-D-lactyl-N-methyl-L-isoleucyl-D-3-amino-phenyllactyl-N-methyl-L-alanyl-D-lactyl-),
cyclo(-N-methyl-L-alanyl-D-lactyl-N-methyl-L-isoleucyl-D-4-amino-phenyllactyl-N-methyl-L-alanyl-D-lactyl-),
cyclo(-N-methyl-L-alanyl-D-lactyl-N-methyl-L-isoleucyl-D-3-morpholino-phenyllactyl-N-methyl-L-alanyl-D-lactyl-),
cyclo(-N-methyl-L-alanyl-D-lactyl-N-methyl-L-isoleucyl-D-4-morpholino-phenyllactyl-N-methyl-L-alanyl-D-lactyl-),
cyclo(-N-methyl-L-alanyl-D-lactyl-N-methyl-L-isoleucyl-D-3-(2-hydroxyethyl-sulphonyl-ethylamino-phenyl)lactyl-N-methyl-L-alanyl-D-lactyl-),
cyclo(-N-methyl-L-alanyl-D-lactyl-N-methyl-L-isoleucyl-D-4-(2-hydroxyethyl-sulphonyl-ethylamino-phenyl)lactyl-N-methyl-L-alanyl-D-lactyl-),
cyclo(-N-methyl-L-alanyl-D-lactyl-N-methyl-L-isoleucyl-D-2-nitro-phenyllactyl-N-methyl-L-2-amino-butyl-D-lactyl-),
cyclo(-N-methyl-L-alanyl-D-lactyl-N-methyl-L-isoleucyl-D-3-nitro-phenyllactyl-N-methyl-L-2-amino-butyl-D-lactyl-),
cyclo(-N-methyl-L-alanyl-D-lactyl-N-methyl-L-isoleucyl-D-4-nitro-phenyllactyl-N-methyl-L-2-amino-butyl-D-lactyl-),
cyclo(-N-methyl-L-alanyl-D-lactyl-N-methyl-L-isoleucyl-D-2-amino-phenyllactyl-N-methyl-L-2-amino-butyl-D-lactyl-),
cyclo(-N-methyl-L-alanyl-D-lactyl-N-methyl-L-isoleucyl-D-3-amino-phenyllactyl-N-methyl-L-2-amino-butyl-D-lactyl-),
cyclo(-N-methyl-L-alanyl-D-lactyl-N-methyl-L-isoleucyl-D-4-amino-phenyllactyl-N-methyl-L-2-amino-butyl-D-lactyl-),
cyclo(-N-methyl-L-alanyl-D-lactyl-N-methyl-L-isoleucyl-D-3-morpholino-phenyllactyl-N-methyl-L-2-amino-butyl-D-lactyl-),
cyclo(-N-methyl-L-alanyl-D-lactyl-N-methyl-L-isoleucyl-D-4-morpholino-phenyllactyl-N-methyl-L-2-amino-butyl-D-lactyl-),
cyclo(-N-methyl-L-alanyl-D-lactyl-N-methyl-L-isoleucyl-D-3-(2-hydroxyethylsulphonyl-ethylamino-phenyl)lactyl-N-methyl-L-2-amino-butyl-D-lactyl-),
cyclo(-N-methyl-L-alanyl-D-lactyl-N-methyl-L-isoleucyl-D-4-(2-hydroxyethylsulphonyl-ethylamino-phenyl)lactyl-N-methyl-L-2-amino-butyl-D-lactyl-),
cyclo(-N-methyl-L-alanyl-D-lactyl-N-methyl-L-isoleucyl-D-2-nitro-phenyllactyl-N-methyl-L-leucyl-D-lactyl-),
cyclo(-N-methyl-L-alanyl-D-lactyl-N-methyl-L-isoleucyl-D-3-nitro-phenyllactyl-N-methyl-L-leucyl-D-lactyl-), cyclo(-N-methyl-L-alanyl-D-lactyl-N-methyl-L-isoleucyl-
D-4-nitro-phenyllactyl-N-methyl-L-leucyl-D-lactyl-),
cyclo(-N-methyl-L-alanyl-D-lactyl-N-methyl-L-isoleucyl-
D-2-amino-phenyllactyl-N-methyl-L-leucyl-D-lactyl-),
cyclo(-N-methyl-L-alanyl-D-lactyl-N-methyl-L-isoleucyl-
D-3-amino-phenyllactyl-N-methyl-L-leucyl-D-lactyl-),
cyclo(-N-methyl-L-alanyl-D-lactyl-N-methyl-L-isoleucyl-
D-4-amino-phenyllactyl-N-methyl-L-leucyl-D-lactyl-),
cyclo(-N-methyl-L-alanyl-D-lactyl-N-methyl-L-isoleucyl-
D-3-morpholino-phenyllactyl-N-methyl-L-leucyl-D-lac-
tyl-),
cyclo(-N-methyl-L-alanyl-D-lactyl-N-methyl-L-isoleucyl-
D-4-morpholino-phenyllactyl-N-methyl-L-leucyl-D-lac-
tyl-),
cyclo(-N-methyl-L-alanyl-D-lactyl-N-methyl-L-isoleucyl-
D-3-(2-hydroxyethylsulphonyl-ethylamino-phenyl)lac-
tyl-N-methyl-L-leucyl-D-lactyl-),
cyclo(-N-methyl-L-alanyl-D-lactyl-N-methyl-L-isoleucyl-
D-4-(2-hydroxyethylsulphonyl-ethylamino-phenyl)lac-
tyl-N-methyl-L-leucyl-D-lactyl-).

The optionally substituted radicals of the general formulae may carry one or more, preferably 1 to 3, in particular 1 to 2, identical or different substituents. The following substituents may be mentioned by way of example and by way of preference:

Alkyl having preferably 1 to 4, in particular 1 to 2, carbon atoms, such as methyl, ethyl, n-propyl, isopropyl, n-butyl, isobutyl, sec-butyl and tert-butyl; alkoxy having preferably 1 to 4, in particular 1 to 2, carbon atoms, such as methoxy, ethoxy, n-propoxy, isopropoxy, n-butoxy, isobutoxy, sec-butoxy and tert-butoxy; alkylthio, such as methylthio, ethylthio, n-propylthio, isopropylthio, n-butylthio, isobutylthio, sec-butylthio; haloalkyl having preferably 1 to 5, in particular 1 to 3, halogen atoms, where the halogen atoms are identical or different and preferably represent fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino; monoalkylamino and dialkylamino having preferably 1 to 4, in particular 1 or 2, carbon atoms per alkyl group, such as methylamino, methylethylamino, dimethylamino, n-propylamino, isopropylamino, methyl-n-butylamino; alkylcarbonyl radicals, such as methylcarbonyl; alkoxycarbonyl having preferably 2 to 4, in particular 2 to 3, carbon atoms, such as methoxycarbonyl and ethoxycarbonyl; alkylsulphinyl having 1 to 4, in particular 1 to 2, carbon atoms; haloalkylsulphinyl having 1 to 4, in particular 1 to 2, carbon atoms and 1 to 5 halogen atoms, such as trifluoromethylsulphinyl; haloalkyl-sulphonyl having 1 to 4, in particular 1 to 2, carbon atoms and 1 to 5 halogen atoms, such as trifluoromethylsulphonyl, perfluoro-n-butyl-sulphonyl, perfluoro-isobutylsulphonyl; arylsulphonyl having preferably 6 or 10 aryl carbon atoms, such as phenylsulphonyl; acyl, aryl, aryloxy which for their part may carry one of the abovementioned substituents and the formimino radical (—HC=N—O-alkyl).

The compounds of the general formula (I) are novel; they can be prepared, for example, by the process given above.

Below, the process according to the invention is illustrated using selected examples (cf. also the Preparation Examples).

If, for example, in process 2a the cyclic depsipeptide cyclo(-N-methyl-L-alanyl-D-lactyl-N-methyl-L-isoleucyl-D-phenyllactyl-N-methyl-L-isoleucyl-D-lactyl-) and fuming nitric acid are used for nitration as compound of the general formula (II) and as nitrating agent, respectively, a mixture of cyclo(-N-methyl-L-alanyl-D-lactyl-N-methyl-L-isoleucyl-D-2-nitro-phenyllactyl-N-methyl-L-isoleucyl-D-lactyl-), cyclo(-N-methyl-L-alanyl-D-lactyl-N-methyl-L-isoleucyl-D-3-nitro-phenyllactyl-N-methyl-L-isoleucyl-D-lactyl-) and cyclo(-N-methyl-L-alanyl-D-lactyl-N-methyl-L-isoleucyl-D-4-nitro-phenyllactyl-N-methyl-L-isoleucyl-D-lactyl-) is formed (cf. Scheme 1).

The formulae (II) provide a general definition of the compounds required as starting materials for carrying out the process 2a. In the formulae (II), $R^1$ to $R^4$ preferably represent those radicals which have already been mentioned in connection with the description of the compounds of the formula (I) according to the invention as being preferred for these substituents.

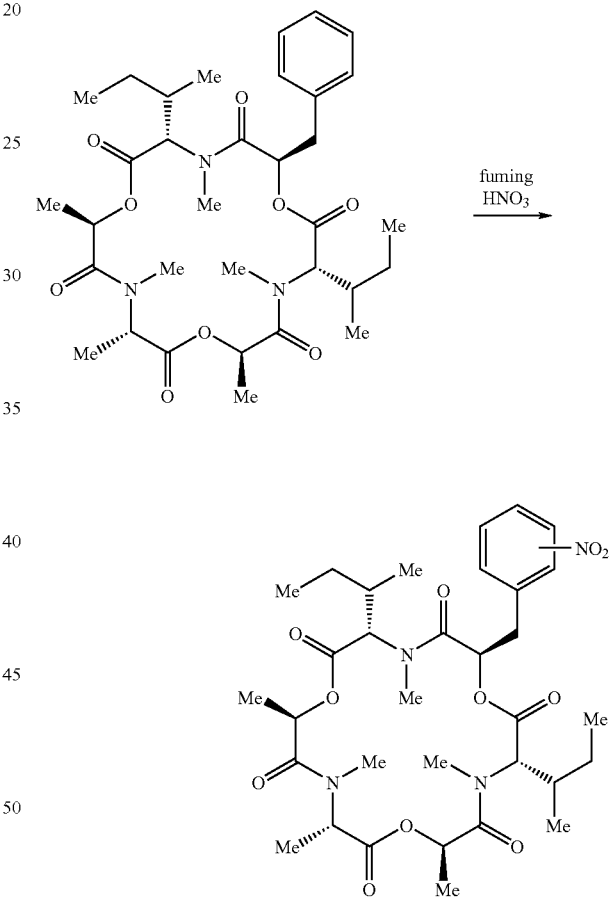

Scheme 1

Some of the cyclic depsipeptides used as starting materials are known, and they can be prepared by total synthesis using methods known from the literature (DE 4317458 A1, EP 658551 A1).

The cyclic depsipeptides of the general formula (II) used as starting materials can be obtained, for example, by cyclization of corresponding open-chain hexadepsipeptides (for example DE 4317458, EP 658551 A1; Jeschke et al. Bioorg. Chem. 1999, pp. 207-214) which can be prepared, for example, by methods known from the literature (for example JP 07196486 A2; open-chain tetradepsipeptides: JP 07196487 A2) (cf. Scheme 2).

Scheme 2

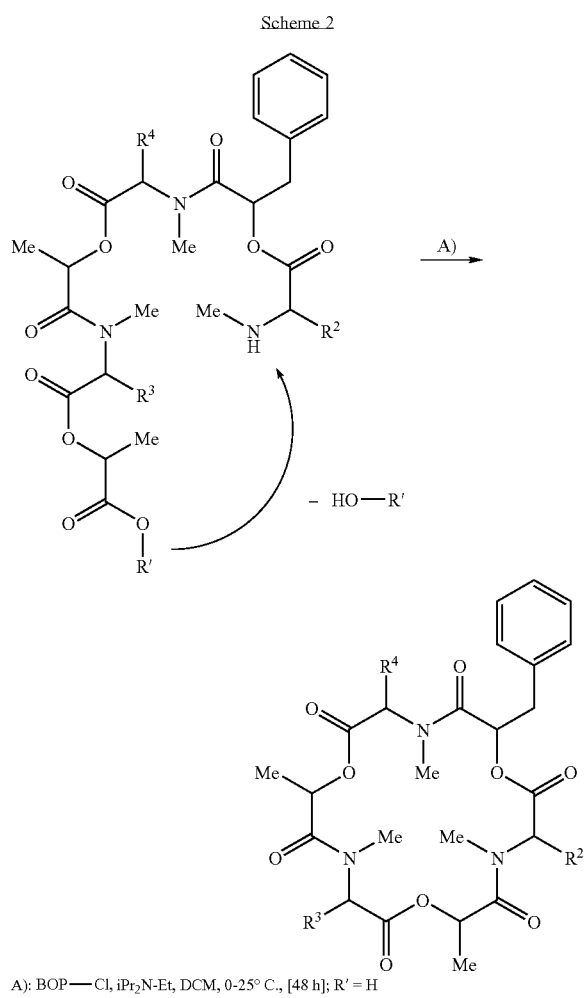

A): BOP—Cl, iPr₂N-Et, DCM, 0-25° C., [48 h]; R' = H

Cyclization of the corresponding open-chain hexadepsipeptides is achieved, for example, using an activated ester (R'=pentafluorophenyl) (cf. also processes for preparing macrocyclic peptide alkaloids: U. Schmidt et al. In Synthesis 1991, pp. 294-300 [didemnin A, B and C]; Angew. Chem. 96, 1984, pp. 723-724 [dolastin 3]; Angew. Chem. 102, 1990, pp. 562-563 [fenestin A]) or, in the case of N,O-terminally deblocked hexadepsipeptides (R'=H) preferably in the presence of coupling agents (cf., for example, Jeschke et al. Bioorg. Chem. 1999, pp. 207-214).

Suitable coupling agents for cyclizing the open-chain hexadepsipeptides are all those which are suitable for generating an amide bond (cf., for example, Houben-Weyl, Methoden der Organischen Chemie, Volume 15/2; Bodansky et al., Peptide Synthesis 2nd ed. (Wiley & Sons, New York 1976) or Gross, Meienhofer, The Peptides: Analysis, Synthesis, Biology (Academic Press, New York 1979)). Preference is given to using the following methods: activated ester method using pentachloro-(Pcp) and pentafluorophenol (Pfp), N-hydroxysuccinimide (HOSu), N-hydroxy-5-norbomene-2,3-dicarboxamide (HONB), 1-hydroxy-benzotriazole (HOBt) or 3-hydroxy-4-oxo-3,4-dihydro-1,2,3-benzotriazine as alcohol component, coupling with carbodiimides, such as dicyclohexylcarbodiimide (DCCI), by the DCC-additive method, or using n-propanephosphoric anhydride (PPA) and the mixed-anhydride method using pivaloyl chloride, ethyl chloroformate (EEDQ) and isobutyl chloroformate (IIDQ), or coupling with phosphonium reagents, such as benzotriazole-1-yl-oxy-tris(dimethylaminophosphonium) hexafluorophosphate (BOP), bis(2-oxo-3-oxazolidinyl)-phosphinic chloride (BOP-Cl), benzotriazol-1-yl-tris-pyrrolidino-phosphonium hexafluorophosphate (PyBOP®), bromo-tris-pyrrolidino-phosphonium hexafluorophosphate (PyBroP®), or using phosphonic ester reagents, such as diethyl cyanophosphonate (DEPC) and diphenylphosphoryl azide (DPPA), uronium reagents, such as 2-(1H-benzotriazol-1-yl)-1,1,3,3-tetramethyluronium tetrafluoroborate (TBTU), 2-(5-norbomene-2,3-dicarboxamido)-1,1,3,3-tetramethyluronium tetrafluoroborate (TNTU), 2-(2-oxo-1(2H)-pyridyl)-1,1,3,3-bispentamethylene-tetramethyluronium tetrafluoroborate (TSTU) or 2-(1H-benzo-triazol-1-yl)-1,1,3,3-tetramethyluronium hexafluorophosphate (HBTU).

Preference is given to coupling with phosphonium reagents, such as bis(2-oxo-3-oxazolidinyl)-phosphinic chloride (BOP-Cl), benzotriazol-1-yl-oxy-tris(dimethylaminophosphonium) hexafluorophosphate (BOP), benzotriazol-1-yl-tris-pyrrolidino-phosphonium hexafluorophosphate (PyBOP®), bromo-tris-pyrrolidinophosphonium hexafluorophosphate (PyBroP®), and phosphonic acid reagents, such as diethyl cyanophosphonate (DEPC) or diphenylphosphoryl azide (DPPA).

Basic reaction auxiliaries suitable for carrying out the cyclization of open-chain hexadepsipeptides are all suitable basic reaction auxiliaries, such as amines, in particular tertiary amines, and alkali metal and alkaline earth metal compounds.

Examples which may be mentioned are the hydroxides, oxides and carbonates of lithium, sodium, potassium, magnesium, calcium and barium, furthermore further basic compounds, such as amidine bases or guanidine bases, such as 7-methyl-1,5,7-triazabicyclo[4.4.0]dec-5-ene (MTBD), diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrrole, N-methylmorpholine, N-methylhexamethyleneimine, pyridine, 4-pyrrolidino-pyridine, 4-dimethylaminopyridine, quinoline, α-picoline, β-picoline, isoquinoline, pyrimidine, acridine, N,N,N',N'-tetramethylenediamine, N,N,N',N'-tetra-ethylenediamine, quinoxaline, N-propyldiisopropylamine, N-ethyldiisopropyl-amine, N,N'-dimethyl cyclohexylamine, 2,6-lutidine, 2,4-lutidine, or triethylenediamine.

Preference is given to using tertiary amines, in particular trialkylamines, such as triethylamine, N,N-diisopropylethylamine, N-propyldiisopropylamine, N,N'-dimethyl cyclohexylamine or N-methylmorpholine.

Nitrations can be carried out by customary processes as described, for example, in Houben-Weyl, Methoden der Organischen Chemie, Volume XI/2 (Georg Thieme Verlag Stuttgart 1958), pp. 99-116. Nitrating agents which may be mentioned are fuming or 100% pure nitric acid (for the preparation of anhydrous nitric acid, cf. F. D. Chattaway, Soc. 1910, 97, p. 2100), if appropriate in the presence of sulphuric acid (M. J. Middleton et al., J. Heterocyclic Chem. 1970, 7, pp. 1045-1049; L. W. Deady et al. Aust. J. Chem. 1982, 35

(10), pp. 2025-2034; EP 0 192 060), or the use of nitric esters, acyl nitrate or nitronium tetrafluoroborate.

The nitrating agents preferably used for carrying out the process 2a according to the invention are fuming or 98-100% pure nitric acid.

The nitration according to process 2a is carried out by reacting the depsipeptides of the general formula (II) in the presence of a suitable nitrating agent, for example fuming nitric acid.

The reaction time is from 5 minutes to 72 hours. The reaction is carried out at temperatures between −50° C. and 50° C., preferably between −30° C. and 30° C., particularly preferably at temperatures between −15° C. and 15° C. In principle, the reaction can be carried out under atmospheric pressure. The operations are preferably carried out at atmospheric pressure or at pressures of up to 15 bar, and, if appropriate, under an atmosphere of protective gas (nitrogen or helium).

For carrying out the process 2a according to the invention, 5 to 10 ml, preferably 6 to ml, of nitrating agent are used per mmole of depsipeptide to be nitrated.

After the nitration has ended, the entire reaction batch is neutralized, diluted and extracted with a suitable organic solvent, for example ethyl acetate. After separation of the organic solvent and concentration under reduced pressure, the resulting products can be purified in a customary manner by recrystallization, vacuum distillation or column chromatography (cf. Preparation Examples).

If, for example in process 2b, the mixture of cyclo(-N-methyl-L-alanyl-D-lactyl-N-methyl-L-isoleucyl-D-2-nitro-phenyl-lactyl-N-methyl-L-isoleucyl-D-lactyl-), cyclo(-N-methyl-L-alanyl-D-lactyl-N-methyl-L-isoleucyl-D-3-nitro-phenyl-lactyl-N-methyl-L-isoleucyl-D-lactyl-), and cyclo(-N-methyl-L-alanyl-D-lactyl-N-methyl-L-isoleucyl-D-4-nitro-phenyllactyl-N-methyl-L-isoleucyl-D-lactyl-) is subsequently used as compounds of the general formula (III) for reduction and hydrogen in the presence of a suitable catalyst, for example palladium hydroxide/carbon, is used as reducing agent, a mixture of cyclo(-N-methyl-L-alanyl-D-lactyl-N-methyl-L-isoleucyl-D-2-amino-phenyllactyl-N-methyl-L-isoleucyl-D-lactyl-), cyclo(-N-methyl-L-alanyl-D-lactyl-N-methyl-L-isoleucyl-D-3-amino-phenyllactyl-N-methyl-L-isoleucyl-D-lactyl-) and cyclo(-N-methyl-L-alanyl-D-lactyl-N-methyl-L-isoleucyl-D-4-amino-phenyllactyl-N-methyl-L-isoleucyl-D-lactyl-) is formed (cf. Scheme 3).

Scheme 3

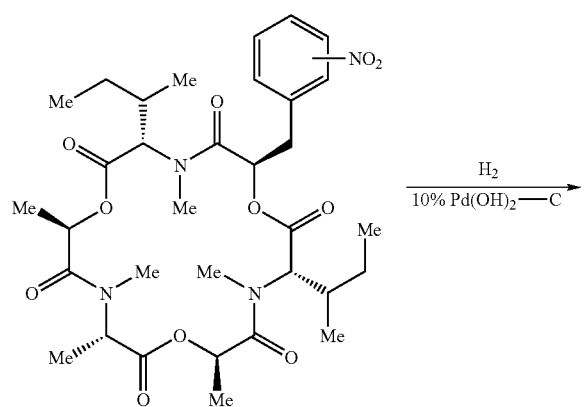

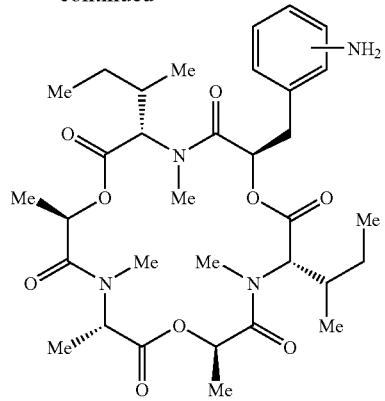

-continued

The formulae (III) provide a general definition of the compounds required as starting materials for carrying out the process 2b. In the formulae (III), $R^1$ to $R^4$ preferably represent those radicals which have already been mentioned in connection with the description of the compounds of the formula (I) according to the invention as being preferred for these substituents.

According to the invention and particularly preferred is the hydrogenolysis of cyclic depsipeptides of the general formula (II) in the presence of a hydrogenation catalyst.

Catalysts suitable for carrying out the catalytic hydrogenation are all customary hydrogenation catalysts, such as, for example, platinum catalysts (platinum plate, platinum sponge, platinum black, colloidal platinum, platinum oxide, platinum wire, etc.), palladium catalysts (for example palladium sponge, palladium black, palladium oxide, palladium/carbon, colloidal palladium, palladium/barium sulphate, palladium/barium carbonate, palladium hydroxide, etc.), ruthenium catalysts, cobalt catalysts (for example reduced cobalt, Raney cobalt, etc.), copper catalysts, (for example reduced copper, Raney copper, Ullman copper, etc.). However, preference is given to using noble metal catalysts, such as, for example, platinum and palladium or ruthenium catalysts, if appropriate on a suitable support, such as, for example, on carbon or silicon.

Preferred hydrogenation catalysts are palladium catalysts, in particular palladium/carbon or palladium hydroxide/carbon.

Generally, it is advantageous to carry out the process 2a according to the invention in the presence of diluents. The diluents are advantageously used in such an amount that the reaction mixture remains easily stirrable during the entire process. Suitable diluents for carrying out the process according to the invention are all inert solvents.

Examples include: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dipropyl ether, diisopropyl ether, di-n-propyl ether, diisopropyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributylamine, N-methyl-morpholine, pyridine and tetramethylenediamine, nitrohydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile, and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl hexyl sulphone, ethyl propyl sulphone, ethyl isobutyl sulphone and pentamethylene sulphone; aliphatic, cycloaliphatic or aromatic hydrocarbons, for example white spirits with components having boiling points in the range for example from 40° C. to 250° C., cymene, benzine fractions within a boiling point range from 70° C. to 190° C., cyclohexane, methyl cyclohexane, petroleum ether, ligroin, octane, benzene, toluene, chlorobenzene, bromobenzene, nitrotoluene, xylene; esters, such as methyl acetate, ethyl acetate, butyl acetate, isobutyl acetate, and dimethyl carbonate, dibutyl carbonate, ethylene carbonate; amides, such as hexamethylenephosphoric triamide, formamide, N-methyl-formamide, N,N-dimethylformamide, N,N-dipropylformamide, N,N-dibutylformamide, N-methyl-pyrrolidine, N-methyl-caprolactam, 1,3-dimethyl-3,4,5,6-tetrahydro-2(1H)-pyrimidine, octylpyrrolidone, octylcaprolactam, 1,3-dimethyl-2-imidazolindione, N-formyl-piperidine, N,N'-1,4-diformylpiperazine; ketones, such as acetone, acetophenone, methyl ethyl ketone, methyl butyl ketone.

The process according to the invention can of course also be carried out in mixtures of the solvents and diluents mentioned.

The diluents to be used depend on the reducing agent employed in each case.

However, alcohols, such as, for example, methanol or ethanol, are preferred diluents for the reduction.

Some of the cyclic depsipeptides used as starting materials are known and can be obtained according to process 2a by nitration.

The reduction according to process 2b is carried out by reacting the depsipeptides of the general formula (III) in the presence of a suitable reducing agent, for example hydrogen in the presence of the catalyst palladium hydroxide/carbon.

The reaction time is from 10 minutes to 72 hours. The reaction is carried out at temperatures between −20° C. and 50° C., preferably between 10° C. and 30° C., particularly preferably at temperatures between −5° C. and 10° C. In principle, the reaction can be carried out under atmospheric pressure. Preferably, the operations are carried out at atmospheric pressure or at pressures of up to 15 bar and, if appropriate, under an atmosphere of protective gas (nitrogen or helium).

For carrying out the process 2b according to the invention, preferably from 0.05 to 1.5 g of reducing agent are employed per mmole of depsipeptide to be reduced.

After the reduction has ended, the reducing agent is removed and the entire reaction batch is concentrated under reduced pressure. The resulting products can be purified in a customary manner by recrystallization, vacuum distillation or column chromatography (cf. Preparation Examples).

If subsequently, for example in process 2c, the pure cyclo (-N-methyl-L-alanyl-D-lactyl-N-methyl-L-isoleucyl-D-4-amino-phenyl-lactyl-N-methyl-L-isoleucyl-D-lactyl-) is used as compounds of the general formula (III) and a suitable dialdehyde, for example HOC—CH$_2$—O—CH$_2$—CHO generated in situ, is used as aldehyde for the aminoalkylation, cyclo(-N-methyl-L-alanyl-D-lactyl-N-methyl-L-isoleucyl-D-4-morpholino-phenyl-lactyl-N-methyl-L-isoleucyl-D-lactyl-) is formed (cf. Scheme 4).

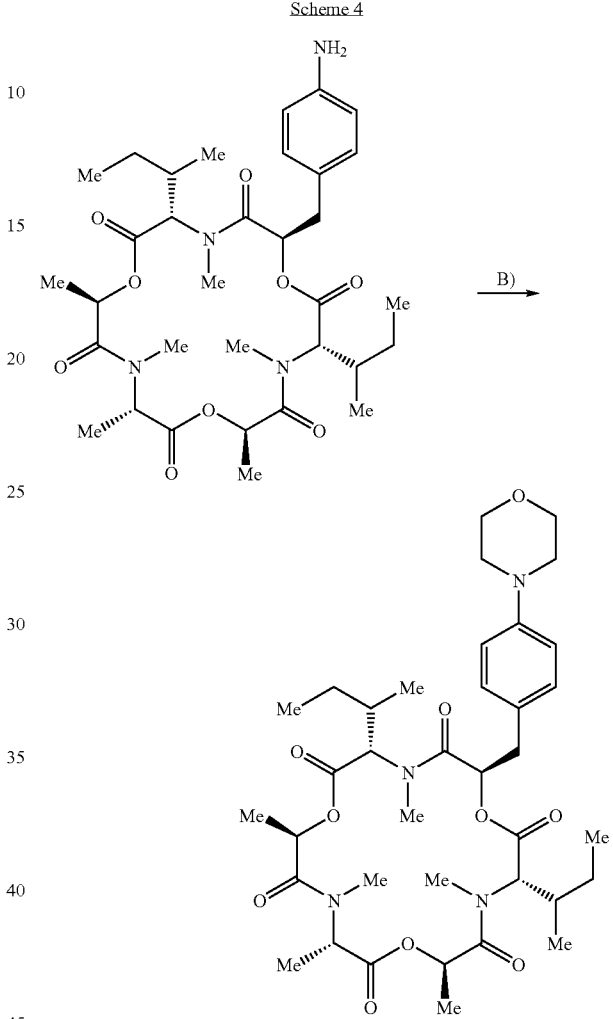

B) in situ [OHC—CH$_2$—O—CH$_2$—CHO], NaCNBH$_3$, methanol, -50° C.

The formulae (IV) provide a general definition of the compounds required as starting materials for carrying out the process 2c. In the formulae (IV), R$^1$ to R$^4$ preferably represent those radicals which have already been mentioned in connection with the description of the compounds of the formula (I) according to the invention as being preferred for these substituents.

The cyclic depsipeptides used as starting materials can be obtained by process 2b.

The dialdehyde used as starting material can be obtained by processes known from the literature, for example (i) by sodium periodate oxidation from 1,4-anhydro-meso-erythritol (E. M. Acton et al. J. Med. Chem. 1984, 27, pp. 638-645), (ii) by hydrolysis of the diketal (RO)$_2$—CH$_2$—O—CH$_2$—(O—R)$_2$ in the presence of 50% strength acetic acid (F. J. Lopez Aparicio et al. Carbohydrat Res. 1982, 111 (1), pp. 157-162; WO 93/10053) or (iii) by ozonolysis from 2,5-dihydrofuran (X=O) (M. Kanemoto Chemistry Express 1987, 2 (1), pp. 17-20) (cf. Scheme 5).

Scheme 5

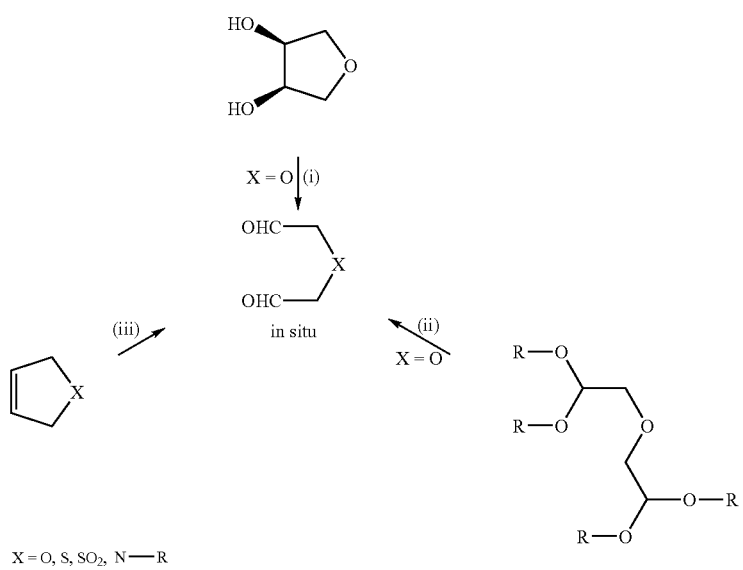

X = O, S, SO₂, N—R

The literature describes a large number of different reducing agents for reductive amination (cf. Houben-Weyl XI/I, p. 602; W. S. Emerson, Org. Reactions 4, 1949, p. 174; E. M. Hancock, A. C. Cope Org. Synth., Coll. Vol. III, 1955, p. 717). Suitable for hydrogenation of the azomethynes formed in situ are, for example, various hydrogenating agents, such as, for example, alkali metal hydrides, in particular sodium borohydride ($NaBH_4$), sodium cyanoborohydride ($NaCNBH_3$), lithium aluminium hydride ($LiAlH_4$), lithium triethylborohydride ($Li[Et_3BH]$), lithium tri-sec-borohydride ($Li[sec-Bu_3BH]$), sodium-bis(2-methoxyethoxy)-aluminium hydride, alkylaluminium hydrides, in particular diisobutylaluminium hydride (DIBAL-H) or tetramethylammoniumtriacetoxy borohydride, inter alia (cf. H. de Koning, W. N. Speckamp, Houben Weyl E 21, p. 1953 and literature cited therein).

It is, of course, also possible to use a "borohydride resin", for example "borohydride on Amberlite® IRA-406", for the hydrogenation (cf. Sande A. R. et al., Tetrahedron Lett. 1984, 25, p. 3501).

For carrying out the process 2c according to the invention, preference is given to using alkali metal hydrides, in particular sodium borohydride ($NaBH_4$), sodium cyanoborohydride ($NaCNBH_3$), lithium aluminium hydride ($LiAlH_4$).

The reductive alkylation according to process 2b is carried out by reacting the depsipeptides of the general formula (III) in the presence of a diluent and in the presence of an aldehyde and a suitable reducing agent, for example sodium cyanoborohydride.

The reaction time is from 10 minutes to 72 hours. The reaction is carried out at temperatures between –20° C. and 50° C., preferably between –10° C. and 30° C., particularly preferably at temperatures between –5° C. and 10° C. In principle, the reaction can be carried out under atmospheric pressure. The operations are preferably carried out at atmospheric pressure or at pressures of up to 15 bar and, if appropriate, under an atmosphere of protective gas (nitrogen or helium).

For carrying out the process 2c according to the invention, preferably from 1.0 mmol to 3.0 mmol of reducing agent are employed per mmole of depsipeptide.

After the aminoalkylation has come to completion, the entire reaction batch is neutralized, diluted and extracted with an organic solvent, for example a chlorinated hydrocarbon. After washing of the organic phase, drying and concentrating under reduced pressure, the resulting products can be purified in a customary manner by recrystallization, vacuum distillation or column chromatography (cf. Preparation Examples).

If, in a further embodiment of the process 2c, the pure cyclo(-N-methyl-L-alanyl-D-lactyl-N-methyl-L-isoleucyl-D-4-amino-phenyl-lactyl-N-methyl-L-isoleucyl-D-lactyl-) is used as compounds of the general formula (III) and a dialdehyde, for example HOC—$CH_2$—$SO_2$—$CH_2$—CHO, is used as aldehyde for the aminoalkylation, surprisingly and according to the invention, cyclo(-N-methyl-L-alanyl-D-lactyl-N-methyl-L-isoleucyl-D-4-(2-hydroxyethylsulphonyl-ethylamino-phenyl)lactyl-N-methyl-L-isoleucyl-D-lactyl-) is formed (cf. Scheme 6).

Scheme 6

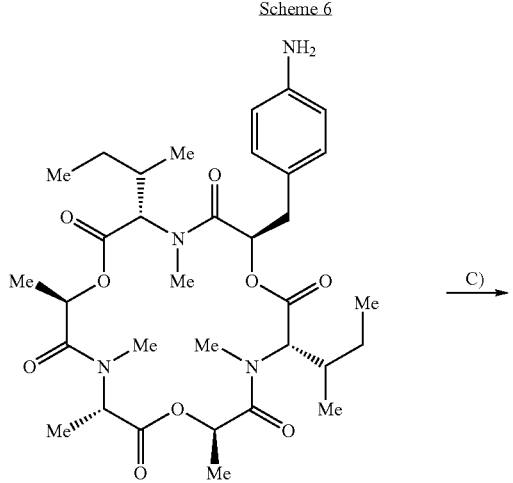

C)

-continued

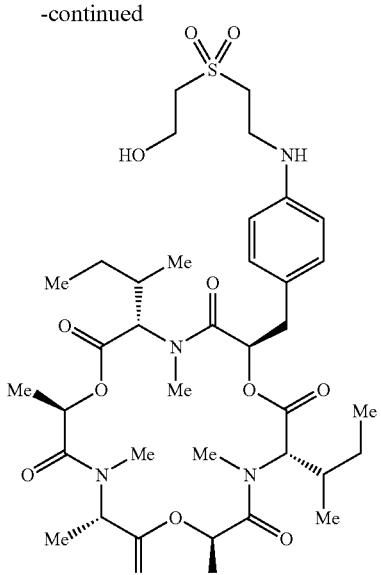

C) in situ [OHC—CH$_2$—SO$_2$—CH$_2$—CHO], NaCNBH$_3$, methanol, -50° C.

The formulae (IV) provide a general definition of the compounds required as starting materials for carrying out the process 2c. In the formulae (IV), $R^1$ to $R^4$ preferably represent those radicals which have already been mentioned in connection with the description of the compounds of the formula (I) according to the invention as being preferred for these substituents.

The cyclic depsipeptides used as starting materials can be obtained according to process 2b.

The dialdehyde used as starting material can be obtained according to process (iii) in Scheme 5, which is known from the literature, by ozonolysis from 3-sulpholes (X=SO$_2$).

The reductive alkylation according to process 2c is carried out by reacting the depsipeptides of the general formula (III) in the presence of a solvent and in the presence of an aldehyde and a suitable reducing agent, for example sodium cyanoborohydride.

The reaction time is from 10 minutes to 72 hours. The reaction is carried out at temperatures between −20° C. and 50° C., preferably between −10° C. and 30° C., particularly preferably at temperatures between −5° C. and 10° C. In principle, the reaction can be carried out under atmospheric pressure. The operations are preferably carried out at atmospheric pressure or at pressures of up to 15 bar and, if appropriate, under an atmosphere of protective gas (nitrogen or helium).

For carrying out the process 2c according to the invention, preferably from 1.0 mmol to 3.0 mmol of reducing agent are employed per mmole of depsipeptide.

After the aminoalkylation has come to completion, the entire reaction batch is neutralized, diluted and extracted with an organic solvent, for example a chlorinated hydrocarbon. After washing of the organic phase, drying and concentrating under reduced pressure, the resulting products can be purified in a customary manner by recrystallization, vacuum distillation or column chromatography (cf. Preparation Examples).

Alternatively and in a further embodiment, the cyclization can also be carried out by reacting the compounds of the general formula (IV) with compounds of the general formula (V), if appropriate in the presence of one of the basic reaction auxiliaries mentioned further above:

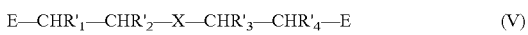

In the compounds of the general formula (V), X preferably represents oxygen, sulphur, sulphonyl or optionally substituted amino, the radicals R'1-R'4 preferably represent $C_1$-$C_2$-alkyl, for example methyl or ethyl, E preferably represents a suitable leaving group, for example halogen, in particular fluorine, chlorine, bromine or iodine, methylsulphonyloxy (Ms-O) or para-toluenesulphonyloxy (p-Tos-O).

The compounds of the general formula (V) are known from the literature and their use, for example for cyclizations, has been described (cf. WO 93/10053). The alkylation is carried out, for example, by reacting the depsipeptides of the general formula (III) in the presence of a solvent and in the presence of a basic reaction auxiliary, according to Scheme 7.

Scheme 7

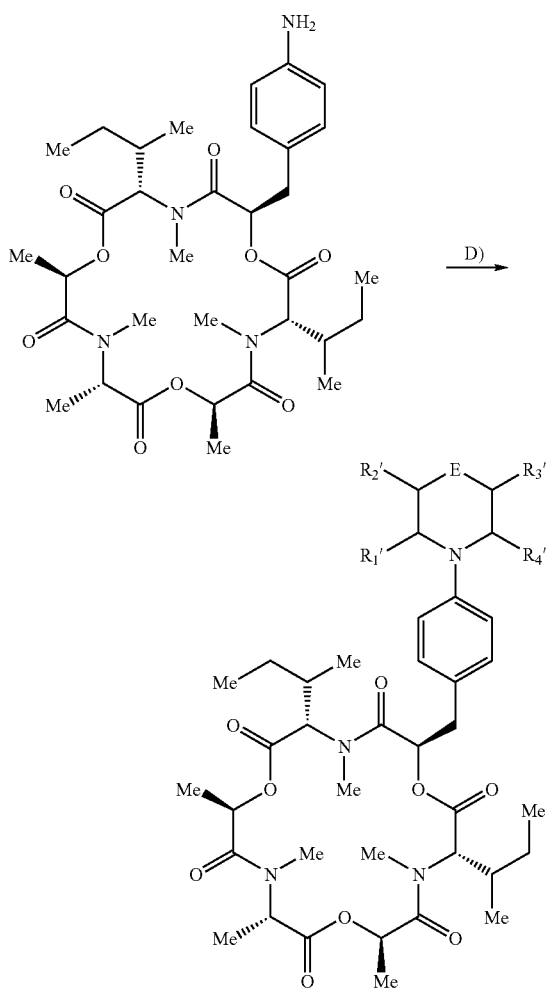

Employing the process 2, cyclic depsipeptides are obtainable, while retaining the original configuration of the starting materials, from the individual building blocks having (S) and (R) configuration (or L and D configuration).

The "inert solvents" in the aforementioned process variants are in each case solvents which are inert under the respective reaction conditions, but which do not have to be inert under all conceivable reaction conditions.

The active compounds are suitable for controlling pathogenic endoparasites encountered in humans and in animal husbandry and livestock breeding, in productive livestock, breeding stock, zoo animals, laboratory animals, animals used in experiments, and pets, and have low toxicity towards warm-blooded animals. Preference is given to application on endoparasites of warm-blooded animals, in particular mammals. They are active against resistant and normally sensitive species and against all or some stages of development of the pests. By controlling the pathogenic endoparasites, it is intended to reduce disease, mortality and decreasing performance (for example in the production of meat, milk, wool, hides, eggs, honey, etc.), so that more economical and simpler animal keeping is possible by using the active compounds. The pathogenic endoparasites include Cestodes, Trematodes, Nematodes, in particular:

From the order of the Pseudophyllidea, for example *Diphyllobothrium* spp., *Spirometra* spp., *Schistocephalus* spp., *Ligula* spp., *Bothridium* spp., *Diphlogonoporus* spp.

From the order of the Cyclophyllidea, for example *Mesocestoides* spp., *Anoplocephala* spp., *Paranoplocephala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

From the subclass of the Monogenea, for example *Gyrodactylus* spp., *Dactylogyrus* spp., *Polystoma* spp.

From the subclass of the Digenea, for example *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp, *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Collyriclum* spp., *Nanophyetus* spp., *Opisthorchis* spp., *Clonorchis* spp., *Metorchis* spp., *Heterophyes* spp., *Metagonimus* spp.

From the order of the Enoplida, for example *Trichuris* spp., *Capillaria* spp., *Trichomosoides* spp., *Trichinella* spp.

From the order of the Rhabditida, for example *Micronema* spp., *Strongyloides* spp.

From the order of the Strongylida, for example *Stronylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp., *Cylicocyclus* spp., *Cylicodontophorus* spp.

From the order of the Oxyurida, for example *Oxyuris* spp., *Enterobius* spp., *Passalurus* spp., *Syphacia* spp., *Aspiculuris* spp., *Heterakis* spp.

From the order of the Ascaridia, for example *Ascaris* spp., *Toxascaris* spp., *Toxocara* spp., *Parascaris* spp., *Anisakis* spp., *Ascaridia* spp.

From the order of the Spirurida, for example *Gnathostoma* spp., *Physaloptera* spp., *Thelazia* spp., *Gongylonema* spp., *Habronema* spp., *Parabronema* spp., *Draschia* spp., *Dracunculus* spp.

From the order of the Filariida, for example *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

From the order of the Gigantorhynchida, for example *Filicollis* spp., *Moniliformis* spp., *Macracanthorhynchus* spp., *Prosthenorchis* spp.

The livestock and breeding stock include mammals, such as, for example, cattle, horses, sheep, pigs, goats, camels, water buffalo, donkeys, rabbits, fallow deer, reindeer, fur-bearing animals, such as, for example, minks, chinchilla or racoon, birds, such as, for example chickens, geese, turkeys or ducks, freshwater fish and sea fish, such as, for example, trout, carp and eels, reptiles and insects, such as, for example, honey bee and silkworm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, tablets, capsules, pastes, drinks, granules, solutions, boluses, medicated feed or drinking water. Dermal application is effected, for example, in the form of dipping, spraying, bathing, washing, pouring-on and spotting-on and powdering. Parenteral administration is effected, for example, in the form of injection (intramuscular, subcutaneous, intravenous or intraperitoneal) or by implants.

Suitable preparations include:

solutions, such as solutions for injection, oral solutions, concentrates for oral administration after dilution, solutions for use on the skin or in body cavities, pour-on formulations, gels;

emulsions and suspensions for oral or dermal administration and for injection; semi-solid preparations;

formulations in which the active compound is incorporated in a cream base or in an oil-in-water or water-in-oil emulsion base;

solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl alcohol, glycerol, hydrocarbons, propylene glycol, polyethylene glycols and N-methyl-pyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active compound.

Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on or are applied by dipping (bathing or washing). These solutions are prepared as described above in the case of the solutions for injection.

It may be advantageous to add thickeners in the preparation process.

The following are thickeners: inorganic thickeners, such as bentonites, colloidal silica, aluminium monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described for the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically or being distributed on the body surface.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethyl-acetamide, N-methylpyrrolidone, or 2,2-dimethyl-4-oxy-methylene-1,3-dioxolane.

Colorants are all colorants which can be dissolved or suspended and which are approved for use in animals.

Examples of absorption promoters are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphite, ascorbic acid, butylhydroxytoluene, butylhydroxyanisole or tocopherol.

Examples of photostabilizers are compounds from the class of the benzophenones and novantisolic acid.

Tackifiers are, for example, cellulose derivatives, starch derivatives, polyacrylates or natural polymers such as alginates or gelatine.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, absorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include:

water, alcohols, such as, for example, propylene glycol, glycerol, sorbitol and their mixtures.

Suitable emulsifiers include: nonionic surfactants, for example polyethoxylated castor oil, polyethoxylated sorbitan monooleate, sorbitan monostearate, glycerol monostearate, polyoxyethyl stearate or alkylphenol polyglycol ethers;

ampholytic surfactants, such as disodium N-lauryl-β-iminodipropionate or lecithin;

anionic surfactants, such as Na lauryl sulphate, fatty alcohol ether sulphates, and the monoethanolamine salt of mono/dialkylpolyglycol ether orthophosphoric ester;

cationic surfactants, such as cetyltrimethylammonium chloride.

Suitable other auxiliaries include: substances which increase the viscosity and stabilize the emulsion, such as carboxymethylcellulose, methylcellulose and other cellulose and starch derivatives, polyacrylates, alginates, gelatine, gum arabic, polyvinyl pyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, absorption promoters, preservatives, antioxidants and photostabilizers.

Suitable liquid excipients include all homogeneous solvents and solvent mixtures.

Suitable wetting agents (dispersants) include the surfactants indicated further above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatine or linear polyvinylpyrrolidone, and dry binders, such as microcrystalline cellulose.

The active compound according to the invention, in its preparations and in the use forms prepared from these preparations, may be present as a mixture with other active compounds such as insecticides, sterilants, bactericides, acaricides, nematicides or fungicides. The insecticides include, for example, phosphoric esters, carbamates, carboxylic esters, chlorinated hydrocarbons, phenylureas, nicotinyls, neonicotinyls, substances produced by microorganisms and the like.

Examples of particularly advantageous components in mixtures are the following:

Fungicides:

aldimorph, ampropylfos, ampropylfos-potassium, andoprim, anilazin, azaconazole, azoxystrobin, benalaxyl, benodanil, benomyl, benzamacril, benzamacryl-isobutyl, bialaphos, binapacryl, biphenyl, bitertanol, blasticidin-s, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromid, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazolecis, furmecyclox, guazatine, hexachlorobenzene, hexaconazole, hymexazol, imazalil, imibenconazole, iminoctadine, iminoctadine-albesilate, iminoctadine triacetate, iodocarb, ipconazole, iprobenfos (IBP), iprodione, irumamycin, isoprothiolane, isovaledione, kasugamycin, kresoxim-methyl, copper preparations such as: copper hydroxide, copper naphthenate, copper oxychloride, copper sulphate, copper oxide, oxine-copper and bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidon, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, tritiN conazole, uniconazole, validamycin A, vinclozolin, viniconazole, zarilamid, zineb, ziram and dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-(α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2, 4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarbox-amide, 2,6-dichloro-5-(methylthio)-4-pyrimidinyl thiocyanate, 2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-9-carbo-2-[(phenylamino)-carbonyl]-hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl-[(4-chlorophenyl)-azo]-cyanoacetate,
potassium hydrogencarbonate,
the sodium salt of methanetetrathiol,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxymethaneimidamide,
the sodium salt of N-formyl-N-hydroxy-DL-alanine,
O,O-diethyl [2-(dipropylamino)-2-oxoethyl]-ethylphosphoramidothioate,
O-methyl S-phenyl phenylpropylphosphoramidothioates,
S-methyl 1,2,3-benzothiadiazole-7-carbothioate,
spiro[2H]-1-benzopyran-2,1'(3'H)-isobenzofuran]-3'-one.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations, quinolones, such as ciprofloxacin, danofloxacin, difloxacin, enrofloxacin, flumequine, ibafloxacin, marbofloxacin, norfloxacin, ofloxacin, orbifloxacin, premafloxacin, sarafloxacin.

Insecticides/Acaricides/Nematicides:

abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, buto-carboxim, butylpyridaben, cadusafos, carbaryl, carbofuran, carbophenothion, carbosulfan, cartap, chloetho-carb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, coumafos, cyanophos, cycloprene, cycloprothrin, cyfluthrin, cyhalothrin, cyhexatin, cypermethrin, cyromazin, cythioate, chlothianidin, deltamethrin, demeton M, demeton S, demeton-S-methyl, diafenthiuron, diazinon, dichlorvos, dicyclanil, diflubenzuron, dimethoate, dimethylvinphos, diofenolan, disulfoton, docusate sodium, dofenapyn, dinotefuran, efusilanate, emamectin, empenthrin, endosulfan, eprinometin, esfenvalerate, ethiofencarb, ethion, ethiprole, ethoprophos, ethofenprox, etoxazole, etrimphos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenthion, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, flupyrazofos, granulosis viruses halofenozide, HCH, heptenophos, hexaflumuron, hexythiazox, hydroprene, imidacloprid, indoxacarb, isazofos, isofenphos, isoxathion, ivermectin, nuclear polyhedrosis viruses lambda-cyhalothrin, lufenuron, malathion, mecarbam, metaldehyde, methamidophos, *Metharhizium anisopliae, Metharhizium flavoviride*, methidathion, methiocarb, methomyl, methoprene, methoxyfenozide, metolcarb, metoxadiazone, metrifonat, mevinphos, milbemectin, monocrotophos, moxidectin, naled, nitenpyram, nithiazine, novaluron, NEEM, omethoate, oxamyl, oxydemethon M,

*Paecilomyces fumosoroseus*, parathion A, parathion M, permethrin, phenthoat, phorat, phosalone, phosmet, phosphamidon, phoxim, pirimicarb, pirimiphos M, pirimiphos A, profenofos, promecarb, propoxur, prothiofos, prothoat, pymetrozine, pyraclofos, pyresmethrin, pyrethrum, pyridaben, pyridathion, pyrimidifen, pyriproxyfen, protrifenbute,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, thiacloprid,
vamidothion, vaniliprole, *Verticillium lecanii*,
YI 5302,
zeta-cypermethrin, zolaprofos,
(1R-cis)-[5-(phenylmethyl)-3-furanyl]-methyl-3-[(dihydro-2-oxo-3(2H)-furanyli-dene)-methyl]-2,2-dimethylcyclopropanecarboxylate
(3-phenoxyphenyl)-methyl-2,2,3,3-tetramethylcyclopropanecarboxylate
1-[(2-chloro-5-thiazolyl)methyl]tetrahydro-3,5-dimethyl-N-nitro-1,3,5-triazine-2(1H)-imine
2-(2-chloro-6-fluorophenyl)-4-[4-(1,1-dimethylethyl)phenyl]-4,5-dihydro-oxazole
2-(acetyloxy)-3-dodecyl-1,4-naphthalenedione
2-chloro-N-[[[4-(1-phenylethoxy)-phenyl]-amino]-carbonyl]-benzamide
2-chloro-N-[[[4-(2,2-dichloro-1,1-difluoroethoxy)-phenyl]-amino]-carbonyl]-benzamide
3-methylphenyl-propylcarbamate
4-[4-(4-ethoxyphenyl)-4-methylpentyl]-1-fluoro-2-phenoxy-benzene
4-chloro-2-(1,1-dimethylethyl)-5-[[2-(2,6-dimethyl-4-phenoxyphenoxy)ethyl]thio]-3(2H)-pyridazinone
4-chloro-2-(2-chloro-2-methylpropyl)-5-[(6-iodo-3-pyridinyl)methoxy]-3(2H)-pyridazinone
4-chloro-5-[(6-chloro-3-pyridinyl)methoxy]-2-(3,4-dichlorophenyl)-3(2H)-pyridazinone
*Bacillus thuringiensis* strain EG-2348
[2-benzoyl-1-(1,1-dimethylethyl)]-benzohydrazide
2,2-dimethyl-3-(2,4-dichlorophenyl)-2-oxo-1-oxaspiro[4,5]dec-3-en-4-yl butanoate
[3-[(6-chloro-3-pyridinyl)methyl]-2-thiazolidinylidene]-cyanamide
dihydro-2-(nitromethylene)-2H-1,3-thiazine-3(4H)-carboxaldehyde
ethyl [2-[[1,6-dihydro-6-oxo-1-(phenylmethyl)-4-pyridazinyl]oxy]ethyl]-carbamate
N-(3,4,4-trifluoro-1-oxo-3-butenyl)-glycine
N-(4-chlorophenyl)-3-[4-(difluoromethoxy)phenyl]-4,5-dihydro-4-phenyl-1H-pyrazole-1-carboxamide
N-[(2-chloro-5-thiazolyl)methyl]-N'-methyl-N"-nitroguanidine
N-methyl-N'-(1-methyl-2-propenyl)-1,2-hydrazinedicarbothioamide
N-methyl-N'-2-propenyl-1,2-hydrazinedicarbothioamide
O,O-diethyl [2-(dipropylamino)-2-oxoethyl]-ethylphosphoramidothioate Furthermore, the active compounds according to the invention may be present, in their commercially available formulations and in the use forms prepared from these formulations, as a mixture with synergists. Synergists are compounds by which the action of the active compounds is increased without it being necessary for the synergist added to be active itself.

Ready-to-use preparations comprise the active compound in concentrations of from 10 ppm to 20% by weight, preferably from 0.1 to 10% by weight.

Preparations which are diluted prior to use comprise the active compound in concentrations of from 0.5 to 90% by weight, preferably from 5 to 50% by weight.

In general, it has been found advantageous to administer amounts of from about 1 to 100 mg of active compound per kg of bodyweight per day to obtain effective results.

EXAMPLES

Preparation Examples

Example I-1

Cyclo(-N-methyl-L-alanyl-D-lactyl-N-methyl-L-isoleucyl-D-4-morpholino-phenyllactyl-N-methyl-L-isoleucyl-D-lactyl-)

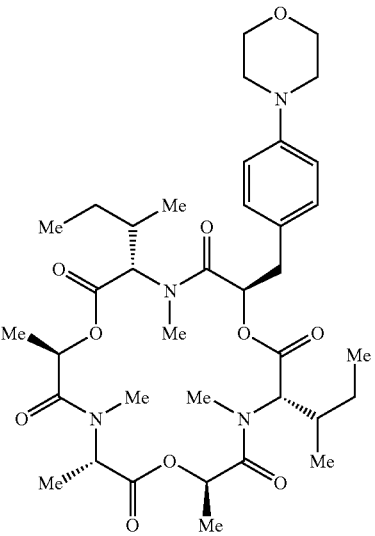

At −60° C., ozone gas is introduced into a mixture of 103 mg (1.47 mmol) of 2,5-dihydrofuran, 0.8 ml of methanol and 3.1 ml of dichloromethane until the reaction mixture has a bluish colour (olefin consumption). Excess ozone is then flushed out in a stream of argon (which is passed through potassium iodide). 185 mg (2.94 mmol) of sodium cyanoborohydride are added to the solution, and the reaction mixture is stirred at −50° C. for 10 minutes. A solution of 650 mg (1.00 mmol) of cyclo(-N-methyl-L-alanyl-D-lactyl-N-methyl-L-isoleucyl-D-4-amino-phenyl-lactyl-N-methyl-L-isoleucyl-D-lactyl-) in 3.9 ml of methanol is then added dropwise, and stirring is continued at 0° C. for 20 hours. The reaction is quenched with 59 mg (0.98 mmol) of acetic acid. After removal of the solvent under reduced pressure, 7.5 ml of saturated sodium bicarbonate solution are added. The reaction mixture is extracted 3 times with 7.5 ml of dichloromethane. The organic phase is then washed using saturated sodium chloride solution and dried over sodium sulphate. Following concentration under reduced pressure, the residue that remains is chromatographed on silica gel using the mobile phase mixture cyclohexane:acetone (2:1) (silica gel 60-Merck, 0.04-0.063 mm). This gives 200 mg (27.7% of theory) of cyclo(-N-methyl-L-alanyl-D-lactyl-N-methyl-L-isoleucyl-D-4-morpholino-phenyl-lactyl-N-methyl-L-isoleucyl-D-lactyl-).

HPLC (0.1% phosphoric acid/acetonitrile; gradient: 90/10 (1) 5%/min, 5/95 (6); flow rate: 1.5 mil/min; UV: 210 nm): $R_t$=12.57 min; log P value 3.58.

$^1$H-NMR (CDCl$_3$, δ): 3.10 (m, 4H, CH$_2$—N—CH$_2$—); 3.85 (m, 4H, CH$_2$—O—CH$_2$—) ppm.

$^{13}$C-NMR (CDCl$_3$, δ): 10.5, 10.7, 13.4, 15.5, 15.6, 16.0, 16.9 (7×CH$_3$); 29.9, 32.2 (CH$_2$); 32.6, 34.2 (2×CH); 30.8, 32.6, 34.2 (3×NCH$_3$); 36.4 (CH$_2$Ph); 49.4 (2×NCH$_2$); 55.9, 59.5, 61.1 (3×NCH); 66.8 (2×OCH$_2$); 66.0, 67.5, 70.0 (3×OCH); 115.7, 130.4 (4×Ph—C); 126.2 (Ph—C); 150.2 (Ph—C—Mor); 170.2, 170.3, 170.5 (3×O—C=O); 168.2, 168.6, 169.6 (3×N—C=O) ppm.

EI-MS m/z (%): 716 (M$^+$, 100), 176 (42).

Example I-2

Cyclo(-N-methyl-L-alanyl-D-lactyl-N-methyl-L-isoleucyl-D-4-(2-hydroxyethyl-sulphonyl-ethylamino-phenyl)lactyl-N-methyl-L-isoleucyl-D-lactyl-)

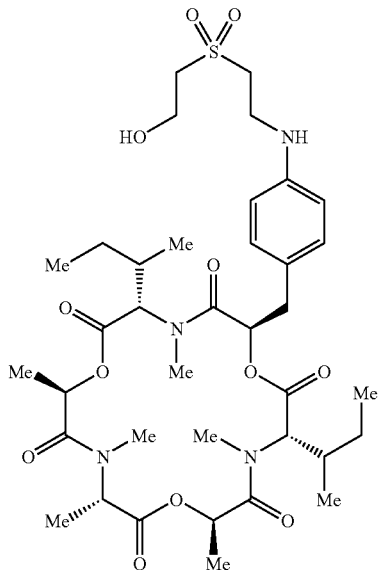

At −60° C., ozone gas is introduced into a mixture of 80.16 mg (0.67 mmol) of 3-sulpholene, 0.36 ml of methanol and 1.44 ml of dichloromethane until the reaction mixture has a bluish colour (olefin consumption). Excess ozone is then flushed out in a stream of argon (which is passed through potassium iodide). 82.26 mg (1.36 mmol) of sodium cyanoborohydride are added to the solution, and the reaction mixture is stirred at −50° C. for 10 minutes. A solution of 650 mg (1.00 mmol) of cyclo(-N-methyl-L-alanyl-D-lactyl-N-methyl-L-isoleucyl-D-4-amino-phenyllactyl-N-methyl-L-isoleucyl-D-lactyl-) in 1.8 ml of absolute methanol is then added dropwise, and stirring is continued at 0° C. for 20 hours. The reaction is quenched with 27.13 mg of acetic acid. After removal of the solvent under reduced pressure, 7.5 ml of saturated sodium bicarbonate solution are added. The reaction mixture is extracted 3 times with 7.5 ml of dichloromethane. The organic phase is then washed with saturated sodium chloride solution and dried over sodium sulphate. Following concentration under reduced pressure, the residue that remains is chromatographed on silica gel using the mobile phase mixture cyclohexane:acetone (1:2) (silica gel 60-Merck, 0.04-0.063 mm). This gives 90 mg (24.8% of theory) of cyclo(-N-methyl-L-alanyl-D-lactyl-N-methyl-L-isoleucyl-D-4-(2-hydroxyethyl-sulphonylethylamino-phenyl)-lactyl-N-methyl-L-isoleucyl-D-lactyl-).

$^1$H-NMR (CDCl$_3$, δ): 3.30 (m, 2H, CH$_2$—OH); 3.46 (m, 2H, NH—CH$_2$—); 3.69 (m, 2H, SO$_2$—CH$_2$—); 4.11 (m, 2H, CH$_2$—SO$_2$—) ppm.

$^{13}$C-NMR (CDCl$_3$, δ): 10.5, 10.5, 13.7, 15.4, 15.5, 16.3, 16.6 (7×CH$_3$); 24.7, 25.0 (CH$_2$); 30.8, 31.7 (2×CH); 32.7, 32.9, 33.9 (3×NCH$_3$); 37.5 (CH$_2$Ph); 37.5 (HNCH$_2$); 53.7, 56.3 (2×SO$_2$CH$_2$); 56.3 (CH$_2$OH); 54.6, 59.8, 60.7 (3×NCH); 66.5, 67.2, 70.4 (3×OCH); 113.1, 130.5 (4×Ph—C); 124.1 (Ph—C); 146.0 (Ph—C—NH); 169.2, 170.3, 170.4, (3×O—C=O); 169.5, 170.4, 170.5 (3×N—C=O) ppm.

negative ESI-MS m/z (%): 781 (M$^+$+H, 36).
positive ESI-MS m/z (%): 781 (M$^+$+H, 42).

Cyclo(-N-methyl-L-alanyl-D-lactyl-N-methyl-L-isoleucyl-D-amino-phenyllactyl-N-methyl-L-isoleucyl-D-lactyl-)

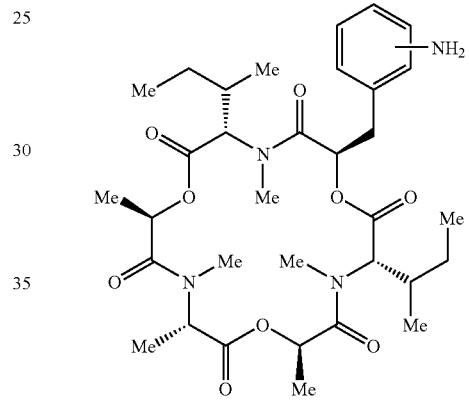

1.0 g (1.48 mmol) of cyclo(-N-methyl-L-alanyl-D-lactyl-N-methyl-L-isoleucyl-D-2-(3- and 4-)-amino-phenyllactyl-N-methyl-L-isoleucyl-D-lactyl-) is stirred in 75 ml of ethanol, 0.15 g of hydrogenation catalyst (20% palladium hydroxide/carbon) is added and the reaction mixture is hydrogenated at room temperature under atmospheric pressure for 4 hours. The catalyst is then filtered off and the solvent is distilled off under reduced pressure. The residue that remains contains an isomer mixture which can be separated by Craig distribution:

| | |
|---|---|
| Apparatus: | 25 ml, 200 distribution elements (from Labortec) |
| Distribution system: | ethyl acetate/n-heptane/DMF/water (4:6:5:5) |
| Phase ratio: | 1 |
| Separation stages: | n = 250, then 300 (circulation) |

Work-up: after the first distribution cycle (n=250) had ended, the contents of every 10th element was removed, the solvents were removed using a rotary evaporator and the residue was weighed and then taken up in 0.5-1.0 ml of acetonitrile and examined by analytical HPLC. The cyclo(-N-methyl-L-alanyl-D-lactyl-N-methyl-L-isoleucyl-D-3-amino-phenyllactyl-N-methyl-L-isoleucyl-D-lactyl-) was found in discharge A1. The contents was removed and, at 40° C., evaporated to dryness using a rotary evaporator. This was followed by a distribution cycle of n=300 (circulation). After the distribution had ended, the contents of elements E 90-130 was removed and concentrated at 40° C. under reduced pressure—this was cyclo(-N-methyl-L-alanyl-D-lactyl-N-methyl-L-isoleucyl-D-4-amino-phenyllactyl-N-methyl-L-isoleucyl-D-lactyl-). In an analogous manner, the corresponding cyclo(-N-methyl-L-alanyl-D-lactyl-N-methyl-L-isoleucyl-D-2-amino-phenyllactyl-N-methyl-L-isoleucyl-D-lactyl-) was obtained from elements E 155-180.

Analytical HPLC:

| | |
|---|---|
| Instrument: | HP 1090 from Hewlett Packard |
| Column: | Kromasil 100, C18, 5 μm, 125 × 4 mm, steel |
| Mobile Phase: | Water/acetonitrile (A/B) |
| Gradient: | A = 90%/B = 10%, 2 min, 5% B/min, A = 5%/B = 95% 6 min isocratic |
| Flow rate: | 1.5 ml/min |
| Detection: | UV, λ = 210 nm |
| Temperature: | 40° C. |
| Injection volume: | 3.5 μl |

Example IV-1

Cyclo(-N-methyl-L-alanyl-D-lactyl-N-methyl-L-isoleucyl-D-2-amino-phenyllactyl-N-methyl-L-isoleucyl-D-lactyl-)

HPLC (0.1% phosphoric acid/acetonitrile; gradient: 90/10 (1) 5%/min, 5/95 (6); flow rate: 1.5 ml/min; UV: 210 nm): $R_t$=11.63 min; log P value 3.18.

$^{13}$C-NMR (CDCl$_3$, δ): 10.2, 10.5, 13.3, 15.5, 15.5, 15.8, 17.1 (7×CH$_3$); 23.9, 24.4 (CH$_2$); 26.8, 30.1 (2×CH); 30.9, 31.5, 32.0 (3×NCH$_3$); 34.0 (CH$_2$Ph); 56.8, 57.9, 60.4 (3×NCH); 65.5, 67.5, 68.9 (3×OCH); 116.1, 118.5, 119.1, 128.0, 131.3 (5×Ph—C); 145.5 (Ph—C—NH$_2$); 168.5, 169.7, 170.3 (3×O—C=O); 168.6, 170.0, 170.8 (3×N—C=O) ppm.

Example IV-2

Cyclo(-N-methyl-L-alanyl-D-lactyl-N-methyl-L-isoleucyl-D-3-amino-phenyllactyl-N-methyl-L-isoleucyl-D-lactyl-)

HPLC (0.1% phosphoric acid/acetonitrile; gradient: 90/10 (1) 5%/min, 5/95 (6); flow rate: 1.5 ml/min; UV: 210 nm): $R_t$=9.32 min; log P value 2.35.

$^{13}$C-NMR (CDCl$_3$, δ): 10.3, 10.5, 13.3, 15.3, 15.5, 15.9, 16.7 (7×CH$_3$); 24.0, 24.6 (CH$_2$); 29.8, 30.7 (2×CH); 32.0, 32.5, 34.0 (3×NCH$_3$); 37.3 (CH$_2$Ph); 55.6, 59.5, 61.0 (3×NCH); 66.0, 67.3, 69.9 (3×OCH); 113.4, 116.1, 119.2, 129.1, 136.1 (5×Ph—C); 146.6 (Ph—C—NH$_2$); 168.2, 169.5, 170.2 (3×O—C=O); 168.6, 170.0, 170.3 (3×N—C=O) ppm.

Example IV-3

Cyclo(-N-methyl-L-alanyl-D-lactyl-N-methyl-L-isoleucyl-D-4-amino-phenyllactyl-N-methyl-L-isoleucyl-D-lactyl-)

HPLC (0.1% phosphoric acid/acetonitrile; gradient: 90/10 (1) 5%/min, 5/95 (6); flow rate: 1.5 ml/min; UV: 210 nm): $R_t$=8.39 min; log P value 2.08.

$^{13}$C-NMR (CDCl$_3$, δ): 10.3, 10.7, 15.4, 15.6, 15.6, 16.0, 16.8 (7×CH$_3$); 24.2, 24.7 (CH$_2$); 30.7, 32.2 (2×CH); 32.6, 33.7, 34.1 (3×NCH$_3$); 36.5 (CH$_2$Ph); 55.7, 59.5, 61.2 (3×NCH); 66.1, 67.4, 70.1 (3×OCH); 115.1, 130.4 (4×Ph—C); 124.9 (Ph—C); 145.2 (Ph—C—NH$_2$); 168.4, 169.6, 170.3 (3×O—C=O); 168.6, 170.2, 170.4 (3×N—C=O) ppm.

Example III-1

Cyclo(-N-methyl-L-alanyl-D-lactyl-N-methyl-L-isoleucyl-D-4-nitro-phenyllactyl-N-methyl-L-isoleucyl-D-lactyl-)

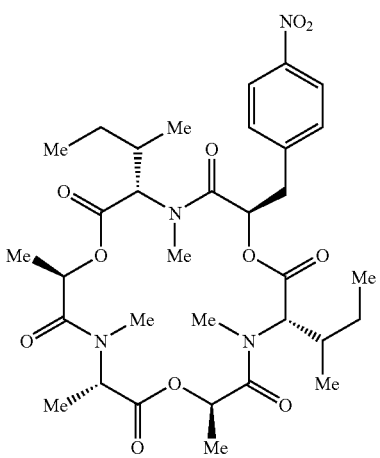

In a flask, 0.5 g (0.79 mmol) of cyclo(-N-methyl-L-alanyl-D-lactyl-N-methyl-L-isoleucyl-D-phenyl-lactyl-N-methyl-L-isoleucyl-D-lactyl-) was cooled to −10° C., and 7 ml of fuming 98% strength nitric acid were added dropwise over a period of 15 minutes. After one hour of stirring at −10° C., the reaction mixture was slowly added to 100 g of ice, and the pH was adjusted to pH 7 using saturated sodium bicarbonate solution. The reaction mixture was then extracted with ethyl acetate. The organic phase was separated off and then washed with saturated sodium chloride solution and again separated off. After drying over sodium sulphate, the solvent was distilled off under reduced pressure. The isomer mixture that remained was purified by preparative HPLC.

m.p.: 122-126° C.

$^{13}$C-NMR (CDCl$_3$, δ): 10.2, 10.5, 15.4, 15.6, 15.6, 15.9, 17.1 (7×CH$_3$); 24.2, 24.5 (CH$_2$); 31.0, 31.5 (2×CH); 32.2, 34.0, 34.0 (3×NCH$_3$); 37.0 (CH$_2$Ph); 56.4, 59.8, 60.3 (3×NCH); 65.6, 67.6, 69.4 (3×OCH); 123.3, 130.3 (4×Ph—C): 143.3 (Ph—C); 146.9 (Ph—C—NO$_2$); 167.2, 169.8, 170.2 (3×O—C=O), 168.2, 169.8, 170.2 (3×N—C=O) ppm.

EI-MS m/z (%): 676 (M$^+$, 28).

X-Ray Structure Analysis:

Single crystals suitable for X-ray analysis can be obtained by recrystallization from a chloroform/n-hexane solvent mixture. The latice constant and the reflex intensities were determined at −80° C. in a Siemens P4 four-circle diffractometer. The structure was resolved using direct methods (programme system SHELXTL). The following structure was determined using the programme SHELXL-93 against F$^2$.

Crystal Data:

| | |
|---|---|
| $C_{33}H_{48}N_4O_{10}$ (660.71 g/mol) | Mo $K_\alpha$ radiation |
| Monoclinic | $\lambda$ = 0.71073 A |
| $P2_1$ | $\mu$ = 0.081 mm$^{-1}$ |
| a = 9.714 (2) A | T = 193 K |
| b = 15.244 (3) A | 0.4 × 0.2 × 0.2 mm |
| c = 14.279 (2) A | prisma colourless |
| $\beta$ = 109.68 (2)° | |
| V = 6237.4 (20) A$^3$ | |
| Z = 2 | |
| $D_x$ = 1.102 Mg/m$^3$ | |

Example II-1

Cyclo(-N-methyl-L-alanyl-D-lactyl-N-methyl-L-isoleucyl-D-phenyllactyl-N-methyl-L-isoleucyl-D-lactyl-)

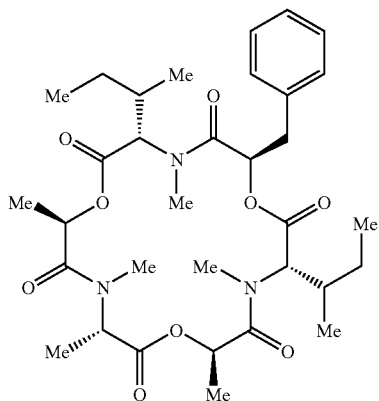

At 0° C., 0.70 g (2.78 mmol) of bis(2-oxo-3-oxazolidinyl)phosphonium chloride (BOP-CI) are added with stirring to a mixture of 1.50 g (2.31 mmol) of N-methyl-L-alanyl-D-lactyl-N-methyl-L-isoleucyl-D-phenyllactyl-N-methyl-L-isoleucyl-D-lactic acid (prepared analogously to DE 4317458, EP 658551 A1; Jeschke et al. Bioorg. Chem. 1999, pp. 207-214) and 0.83 g (6.43 mmol) of N,N-diisopropylethylamine (DIEA) in 500 ml of dichloromethane. After 24 hours of stirring at room temperature, another 0.83 g (6.43 mmol) of DIEA and 0.70 g (2.78 mmol) of BOP-CI are added, and stirring is continued for another 24 hours. The reaction mixture is then washed twice with water and the organic phase is separated off and dried over sodium sulphate. The organic phase is then concentrated under reduced pressure, and the crude product that remains is purified by column chromatography (silica gel 60-Merck, particle size: 0.04-0.063 mm) using the mobile phase mixture toluene/ethyl acetate (2:1). This gives 2.2 g (64.7% of theory) of cyclo(-N-methyl-L-alanyl-D-lactyl-N-methyl-L-isoleucyl-D-phenyllactyl-N-methyl-L-isoleucyl-D-lactyl-).

HPLC (0.1% phosphoric acid/acetonitrile; gradient: 90/10 (1) 5%/min, 5/95 (6); flow rate: 1.5 ml/min; UV: 210 nm): $R_t$=13.94 min; log P value 4.23.

$^{13}$C-NMR (CDCl$_3$, δ): 10.3, 10.7, 13.4, 15.5, 15.6, 16.0, 16.9 (7×CH$_3$); 24.1, 24.7 (CH$_2$); 29.9, 30.7 (2×CH); 32.5, 33.9, 34.2 (3×NCH$_3$); 37.3 (CH$_2$Ph); 55.9, 59.5, 61.1 (3×NCH); 66.0, 67.5, 70.0 (3×OCH); 126.8 (Ph—C); 128.4, 129.6 (4×Ph—C); 135.4 (Ph—C); 168.0, 169.6, 170.3 (3×O—C=O), 168.6, 170.2, 170.5 (3×N—C—O) ppm.

EI-MS m/z (%): 631 (M$^+$, 52), 558 (22), 415 (26), 330 (10), 258 (89), 100 (90).

Biological Examples

Example A

In Vivo Nematode Test

*Haemonchus contortus*/sheep

Sheep which had been experimentally infected with *Haemonchus contortus* were treated after the prepotency time of the parasite had elapsed. The active compounds were applied orally and/or intravenously as pure active compound.

The degree of effectiveness is determined by quantitatively counting the worm eggs which have been excreted with the faeces before and after the treatment.

A complete cessation of egg excretion after the treatment means that the worms have been aborted or damaged to such an extent that they no longer produce eggs (dosis effectiva).

Active compounds tested and effective dosage rates (dosis effectiva) can be seen from the table which follows.

| Active compound/Example No. | Effective dosage [mg/kg] |
|---|---|
| I-1 | 0.10 |
| I-2 | 0.10 |
| IV-1 | 0.05 |
| IV-2 | 0.05 |

Example B

In Vivo Nematode Test

*Trichostrongylus colubriformis*/sheep

Sheep which had been experimentally infected with *Trichostrongylus colubriformis* were treated after the prepotency time of the parasite had elapsed. The active compounds were applied orally and/or intravenously as pure active compound.

The degree of effectiveness is determined by quantitatively counting the worm eggs which have been excreted with the faeces before and after the treatment.

A complete cessation of egg excretion after the treatment means that the worms have been aborted or damaged to such an extent that they no longer produce eggs (dosis effectiva).

Active compounds tested and effective dosage rates (dosis effectiva) can be seen from the table which follows.

| Active compound/Example No. | Effective dosage [mg/kg] |
|---|---|
| I-1 | 0.25 |
| IV-2 | 0.25 |

The invention claimed is:

1. A cyclic depsipeptide of formula (I) or salt thereof

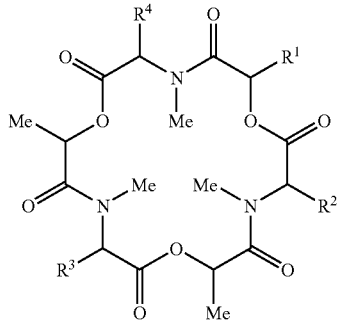

in which
R$^1$ represents nitrobenzyl or R'R"N-benzyl
where
R' and R" independently of one another each represent hydrogen, optionally substituted C$_1$-C$_4$-alkyl, formyl, C$_1$-C$_4$-alkoxy-C$_1$-C$_4$-alkyl, C$_1$-C$_4$-alkoxycarbonyl, hydroxyl-C$_1$-C$_2$-alkylsulphonyl-C$_1$-C$_2$-alkyl,
or
R' and R" together with the nitrogen atom to which they are attached form an optionally substituted mono- or polycyclic saturated or unsaturated heterocycle which is optionally bridged and/or siprocyclic and which contains 1 to 3 further heteroatoms from the group consisting of nitrogen, oxygen and sulphur, or R' and R" together form C$_3$-C$_5$-alkylenemonocarbonyl or an optionally substituted diacyl radical of a C$_4$-C$_6$-dicarboxylic acid, and
R$^2$, R$^3$ and R$^4$ independently of one another represent C$_1$-C$_4$-alkyl, or an optical isomer thereof.

2. The depsipeptide of claim 1
in which
R$^1$ represents nitrobenzyl or R'R"N-benzyl
where
R' and R" independently of one another each represent hydrogen, C$_1$-C$_3$-alkyl, in particular methyl, ethyl, C$_1$-C$_3$-alkoxy-C$_1$-C$_3$-alkyl, in particular methoxyethyl, 2-hydroxyethylsulphonyl-C$_1$-C$_2$-alkyl, in particular 2-hydroxyethylshulphonylethyl, or
R' and R" together with the nitrogen atom to which they are attached represent N-pyrrolidino, N-piperidino, N-piperazino, N-morpholino, N-2,6-dimethylmorpholino, N-thiomorpholino, N-pyrazolo, N-imidazolo, 2-oxopyrrolidin-1-yl, 2-oxopiperidin-1-yl, 2-oxoazepan-1-ylmethyl, succinimino, maleinimino or glutarimino,
R$^2$, R$^3$ and R$^4$ independently of one another represent C$_1$-C$_4$-alkyl, and
or an optical isomer thereof.

3. The depsipeptide of claim 1
in which
R$^1$ represents 4-nitrobenzyl, 4-aminobenzyl, 4-morpholinobenzyl, 4-hydroxyethylsulphonylethylaminobenzyl,
R$^2$ and R$^4$ independently of one another represent C$_1$-C$_4$-alkyl,
R$^3$ represents methyl or ethyl,
or an optical isomer thereof.

4. A process for preparing a cyclic depsipeptide of formula (I) or salts thereof

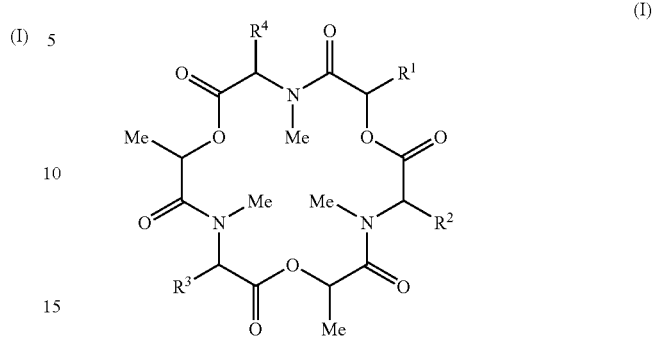

in which
R$^1$, R$^2$, R$^3$ and R$^4$ are as defined in claim 1, which comprises
a. in a first step, nitrating a cyclic depsipeptide of formula (II) or salt thereof

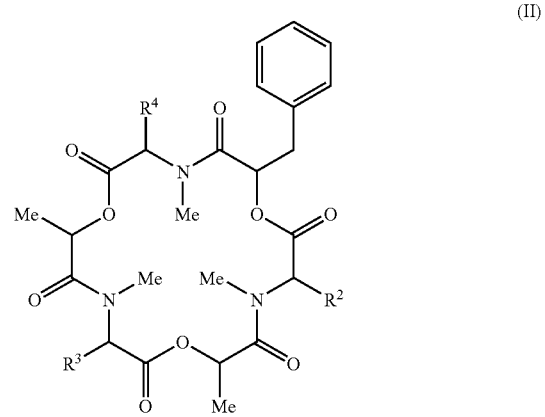

in which
R$^2$, R$^3$ and R$^4$ are as defined in claim 1,
in the presence of a nitrating agent and, if appropriate, in the presence of a diluent, and
b. if appropriate, in a second step, reducing the nitro group in a cyclic depsipeptide of formula (III) or salt thereof obtained in this manner

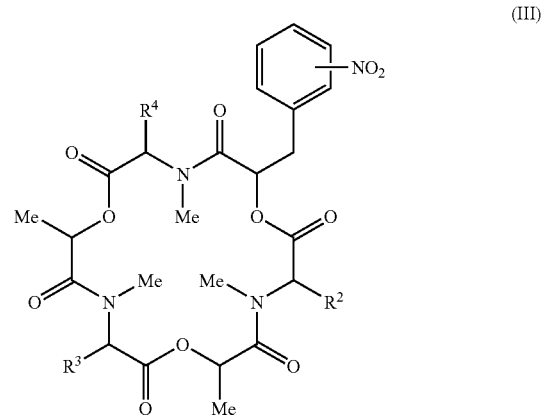

in which
R², R³ and R⁴ are as defined in claim 1,
in the presence of a reducing agent and, if appropriate, in the presence of a diluent, and c. if appropriate, in a third step, aminoalkylating a cyclic depsipeptide of formula (IV) or salt thereof

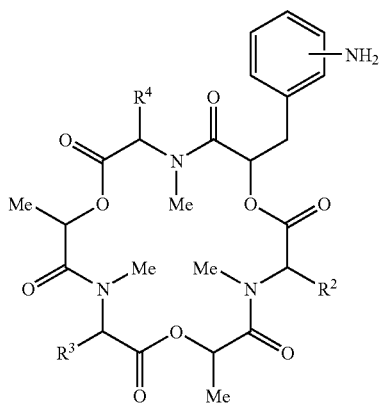

(IV)

in which
R², R³ and R⁴ are as defined in claim 1, to introduce the radicals R' and R", in the presence of a suitable aldehyde and a reducing agent and, if appropriate, in the presence of a diluent, or N-alkylating the depsipeptides in the presence of a suitable alkylating agent and a basic reaction auxiliary and, if appropriate, in the presence of a diluent, or N-acylating the depsipeptides in the presence of a suitable acylating agent and a basic reaction auxiliary and, if appropriate, in the presence of a diluent.

5. A composition comprising a cyclic depsipeptide of claim 1.

6. A method for controlling endoparasites comprising administering to a human or animal in need thereof an effective amount of a cyclic depsipeptide of claim 1.

7. The depsipeptide of claim 1, wherein R² and R⁴ independently of one another are selected from the group consisting of methyl, isopropyl, isobutyl, and sec-butyl.

8. A method for controlling endoparasites comprising applying to a habitat an effective amount of a cyclic depsipeptide of claim 1.

* * * * *